(12) United States Patent
Dreano et al.

(10) Patent No.: US 7,465,441 B2
(45) Date of Patent: Dec. 16, 2008

(54) USE OF GP130 ACTIVATORS IN DIABETIC NEUROPATHY

(75) Inventors: Michel Dreano, Colonges-sous-Saleve (FR); Pierre-Alain Vitte, Cranves-Sales (FR)

(73) Assignee: Laboratoires Serono SA, Vaud (CH)

( * ) Notice: Subject to any disclaimer, the term of this patent is extended or adjusted under 35 U.S.C. 154(b) by 299 days.

(21) Appl. No.: 10/492,087

(22) PCT Filed: Oct. 10, 2002

(86) PCT No.: PCT/EP02/11364

§ 371 (c)(1), (2), (4) Date: Oct. 25, 2004

(87) PCT Pub. No.: WO03/033015

PCT Pub. Date: Apr. 24, 2003

(65) Prior Publication Data

US 2005/0058623 A1 Mar. 17, 2005

(30) Foreign Application Priority Data

Oct. 11, 2001 (EP) .................................. 01123400

(51) Int. Cl.
*A61K 38/20* (2006.01)
*A61K 38/16* (2006.01)
*A61K 38/17* (2006.01)
*A61K 38/19* (2006.01)

(52) U.S. Cl. .................. 424/85.2; 424/85.1; 514/12

(58) Field of Classification Search .................. None
See application file for complete search history.

(56) References Cited

U.S. PATENT DOCUMENTS 6,054,294 A 4/2000 Chang
6,479,258 B1 * 11/2002 Short .................... 435/69.1

FOREIGN PATENT DOCUMENTS

WO WO 95/00852 A 1/1995
WO WO 96/27672 A 9/1996
WO WO 01/03737 A 1/2001

OTHER PUBLICATIONS

Müller-Newen, G. (2003). The cytokine receptor gp130: faithfully promiscuous. Science's STKE. PE40:1-3.*

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era. Trends in Biotechnology. 18:34-39.*
Vincent et al. (2004). New insights into the mechanisms of diabetic neuropathy. Reviews in Endocrine and Metabolic Disorders. 5:227-236.*
Phillips, A.J. (2001). The challenge of gene therapy and DNA delivery. Journal of Pharmacy and Pharmacology. 53:1169-1174.*
Palù et al. (1999). In pursuit of new developments for gene therapy. Journal of Biotechnology. 68:1-13.*
Senaldi et al. (1999). Novel neurotrophin-1/B cell-stimulating factor-3: a cytokine of the IL-6 family. Proc. Natl. Acad. Sci. USA. 96(20):11458-11463.*
Federico, M. "Lentiviruses as gene delivery vectors" *Current Opinion in Biotechnology* 10 pp. 448-453 (1999).
Loddick et al "Interleukin-1 receptors: cloning studies and role in central nervous system disorders" *Brain Research Reviews* 26 pp. 306-319 (1998).
Ma et al "Neurotoxic Effects of Interleukin-6 and Sodium Nitroprusside on Cultured Rat Hippocampal Neurons" *Arzneim.-Forsch./Drug Res.* 50 (I), Nr. 6 pp. 512-514 (2000).
Pittenger et al "IL6 Blocks Neurotoxicity of Diabetic Neuropathy Patients' Sera on Neuropblastoma Cells" *Diabetes*, 48 pp. A384 (1998).
Schafer et al "The IL-6/IL-6R Fusion Protein Hyper IL-6 Promotes Neurite Outgrowth and Neuron Survival in Cultured Enteric Neurons" *Journal of Interferon and Cytokine Research* 19 pp. 527-532. (1999).
Takizawa et al "Directly Linked Soluble IL-6 Receptor-IL-6 Fusion Protein Induces Astrocyte Differenctiation From Neuropithelial Cells via Activation of STAT3" *Cytokine*, vol. 13, No. 5 (Mar. 7, 2001) pp. 272-279.
Van Wagoner et al "Interleukin-6 (IL-6) Production by Astrocytes: Autocrine Regulation by IL-6 and the Soluble IL-6 Receptor" *The Journal of Neuroscience*, 19(13) pp. 5236-5244 (1991).
Vinik A I et al "Diabetic Neuropathies" *Diabetes Care, American Diabetes Association* 15(12): pp. 1926-1975 (1992).
Vinik et al "Neuroptrophic factors in diabetic neuropathy" *Current Opinion in Endocrinology and Diabetes* 8(4), pp. 205-212 (2001).

* cited by examiner

*Primary Examiner*—Christine J Saoud
*Assistant Examiner*—Jon M Lockard
(74) *Attorney, Agent, or Firm*—Browdy and Neimark, P.L.L.C.

(57) ABSTRACT

The invention relates to the use a substance signaling through gp130 for the manufacture of a medicament for the treatment and/or prevention of diabetic neuropathy. The use of IL-6 is preferred.

17 Claims, 26 Drawing Sheets

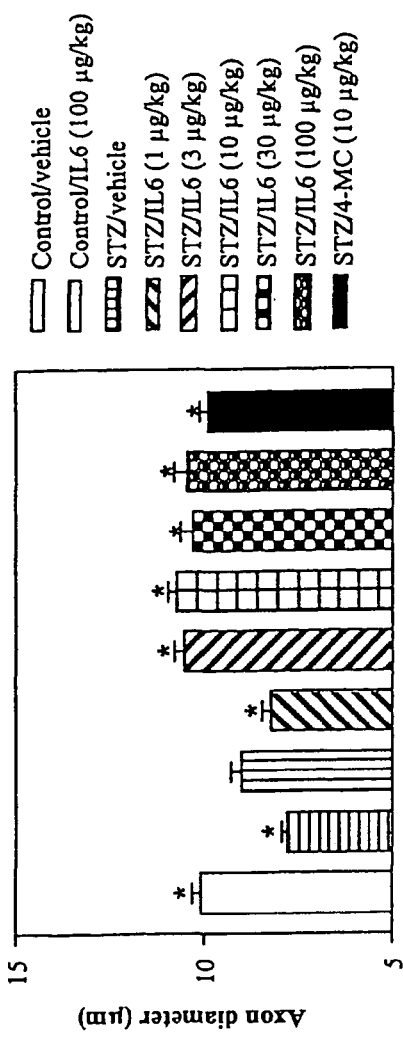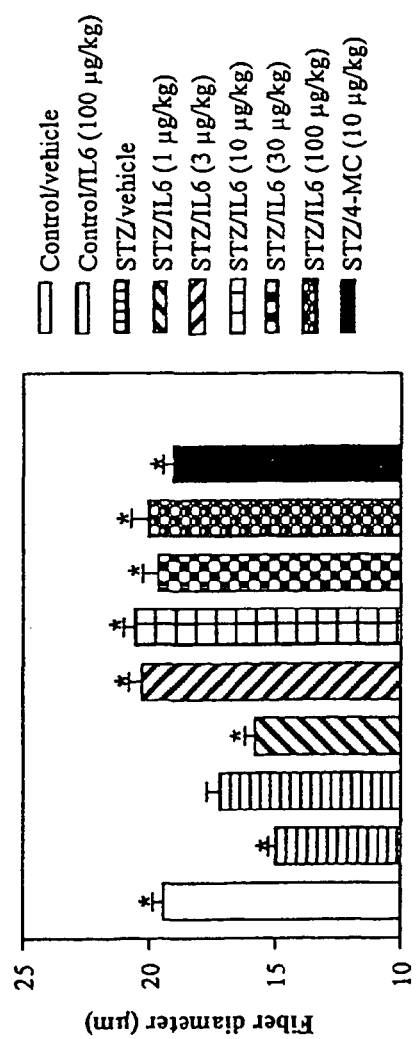
Fig. 6
Fig. 7

USE OF GP130 ACTIVATORS IN DIABETIC NEUROPATHY

FIELD OF THE INVENTION

The present invention is in the field of diabetes mellitus and peripheral nervous system disorders. In particular, it relates to the use of substances signaling through gp130 for the manufacture of a medicament for the treatment and/or prevention of diabetic neuropathy. IL-6, or an IL-6R/IL-6 chimera are preferably used in this specific medical indication.

BACKGROUND OF THE INVENTION

Diabetes mellitus is a disorder of carbohydrate metabolism, i.e. a syndrome characterized by hyperglycemia resulting from absolute or relative impairment in insulin secretion and/or insulin action.

Classification of Diabetes mellitus is based on the one adopted by the National Diabetes Data Group and WHO. Previously, it was based on age at onset, duration, and complications of the disease. Gestational diabetes mellitus is carbohydrate intolerance of variable severity with onset or first recognition during the current pregnancy. Patients with type I diabetes mellitus (DM), also known as insulin-dependent DM (IDDM) or juvenile-onset diabetes, may develop diabetic ketoacidosis (DKA). Patents with type II DM, also known as non-insulin-dependent DM (NIDDM), may develop nonketotic hyperglycemic-hyperosmolar coma (NKHHC). Common late microvascular complications include retinopathy, nephropathy, and peripheral and autonomic neuropathies. Macrovascular complications include atherosclerotic coronary and peripheral arterial disease.

Type I diabetes mellitus: Although it may occur at any age, type I diabetes mellitus most commonly develops in childhood or adolescence and is the predominant type of DM diagnosed before age 30. This type of diabetes accounts for 10 to 15% of all cases of DM and is characterized clinically by hyperglycemia and a propensity to diabetic ketoacidosis. The pancreas produces little or no insulin.

About 80% of patients with type I DM have specific HLA phenotypes associated with detectable serum islet cell cytoplasmic antibodies and islet cell surface antibodies (antibodies to glutamic acid decarboxylase and to insulin are found in a similar proportion of cases).

In these patients, type I DM results from a genetically susceptible, immune-mediated, selective destruction of >90% of their insulin-secreting cells. Their pancreatic islets exhibit insulitis, which is characterized by an infiltration of T lymphocytes accompanied by macrophages and B lymphocytes and by the loss of most of the beta-cells, without involvement of the glucagon-secreting alpha-cells. The antibodies present at diagnosis usually become undetectable after a few years. They may be primarily a response to beta-cell destruction, but some are cytotoxic for beta-cells and may contribute to their loss. The clinical onset of type I DM may occur in some patients years after the insidious onset of the underlying autoimmune process. Screening for these antibodies is included in numerous ongoing preventive studies.

Type II diabetes mellitus: Type II DM is usually the type of diabetes diagnosed in patients >30 years, but it also occurs in children and adolescents. It is characterized clinically by hyperglycemia and insulin resistance. Diabetic ketoacidosis is rare. Although most patients are treated with diet, exercise, and oral drugs, some patients intermittently or persistently require insulin to control symptomatic hyperglycemia and prevent nonketotic hyperglycemic-hyperosmolar coma. The concordance rate for type II DM in monozygotic twins is >90%. Type II DM is commonly associated with obesity, especially of the upper body (visceral/abdominal), and often present after a period of weight gain. Impaired glucose tolerance associated with aging is closely correlated with the typical weight gain. Type II DM patients with visceral/abdominal obesity may have normal glucose levels after losing weight.

Type II DM is a heterogeneous group of disorders in which hyperglycemia results from both an impaired insulin secretory response to glucose and decreased insulin effectiveness in stimulating glucose uptake by skeletal muscle and in restraining hepatic glucose production (insulin resistance). However, insulin resistance is common, and most patients with insulin resistance will not develop diabetes, because the body compensates by adequately increasing insulin secretion. Insulin resistance in the common variety of type II DM is not the result of genetic alterations in the insulin receptor or the glucose transporter. However, genetically determined post-receptor intracellular defects likely play a role. The resulting hyperinsulinemia may lead to other common conditions, such as obesity (abdominal), hypertension, hyperlipidemia, and coronary artery disease (the syndrome of insulin resistance).

Genetic factors appear to be the major determinants for the development of type II DM, yet no association between type II DM and specific HLA phenotypes or islet cell cytoplasmic antibodies has been demonstrated. An exception is a subset of non-obese adults with detectable islet cell cytoplasmic antibodies who carry one of the HLA phenotypes and who may eventually develop type I DM.

Before diabetes develops, patients generally lose the early insulin secretory response to glucose and may secrete relatively large amounts of proinsulin. In established diabetes, although fasting plasma insulin levels may be normal or even increased in type II DM patients, glucose-stimulated insulin secretion is clearly decreased. The decreased insulin levels reduce insulin-mediated glucose uptake and fail to restrain hepatic glucose production.

Hyperglycemia may not only be a consequence but also a cause of further impairment in glucose tolerance in the diabetic patient (glucose toxicity) because hyperglycemia decreases insulin sensitivity and increases hepatic glucose production. Once a patient's metabolic control improves the insulin or hypoglycemic drug dose is usually lowered.

Some cases of type II DM occur in young, non-obese adolescents (maturity-onset diabetes of the young [MODY]) with an autosomal dominant inheritance. Many families with MODY have a mutation in the glucokinase gene. Impairments in insulin secretion and in hepatic glucose regulation have been demonstrated in these patients.

Insulinopathies are rare cases of DM, with the clinical characteristics of type II DM, result from the heterozygous inheritance of a defective gene, leading to secretion of insulin that does not bind normally to the insulin receptor. These patients have greatly elevated plasma immunoreactive insulin levels associated with normal plasma glucose responses to exogenous insulin.

Diabetes may also be attributed to pancreatic disease: Chronic pancreatitis, particularly in alcoholics, is frequently associated with diabetes. Such patients lose both insulin-secreting and glucagon-secreting islets. Therefore, they may be mildly hyperglycemic and sensitive to low doses of insulin. Given the lack of effective counterregulation (exogenous insulin that is unopposed by glucagon), they frequently suffer from rapid onset of hypoglycemia. In Asia, Africa, and the Caribbean, DM is commonly observed in young, severely malnourished patients with severe protein deficiency and pancreatic disease; these patients are not prone to diabetic ketoacidosis but may require insulin.

Diagnosis of diabetes mellitus: In asymptomatic patients, DM is established when the diagnostic criterion for fasting hyperglycemia is met: a plasma (or serum) glucose level of >=140 mg/dl (>=7.77 mmol/l) after an overnight fast on two occasions in an adult or child.

An oral glucose tolerance test may be helpful in diagnosing type II DM in patients whose fasting glucose is between 115 and 140 mg/dl (6.38 and 7.77 mmol/L) and in those with a clinical condition that might be related to undiagnosed DM (e.g. polyneuropathy, retinopathy).

Treatment of diabetes mellitus: Hyperglycemia is responsible for most of the long-term microvascular complications of diabetes. It demonstrated a linear relationship between the levels of Hb $A_{1c}$ (see below) and the rate at which complications developed. Other studies have suggested that Hb $A_{1c}$<8% is a threshold below which most complications can be prevented. Thus, therapy for type I DM should try to intensify metabolic control to lower Hb $A_{1c}$ while avoiding hypoglycemic episodes. However, treatment must be individualized and should be modified when circumstances make any risk of hypoglycemia unacceptable (e.g. in patients with a short life expectancy and in those with cerebrovascular or cardiac disease) or when the patient's risk of hypoglycemia is increased (e.g. in patients who are unreliable or who have autonomic neuropathy).

Diet to achieve weight reduction is most important in overweight patients with type II DM. If improvement in hyperglycemia is not achieved by diet, trial with an oral drug should be started.

The patient should be regularly assessed for symptoms or signs of complications, including a check of feet and pulses and sensation in the feet and legs, and a urine test for albumin. Periodic laboratory evaluation includes lipid profile, BUN (blood urea nitrogen) and serum creatinine levels, ECG, and an annual complete ophthalmologic evaluation.

Hypercholesterolemia or hypertension increases the risks for specific late complications and requires special attention and appropriate treatment. Although beta-adrenergic receptor blocking agents β-blockers, such as propranolol) can be used safely in most diabetics, they can mask the β-adrenergic symptoms of insulin-induced hypoglycemia and can impair the normal counterregulatory response. Thus, ACE inhibitors and calcium antagonists are often the drugs of choice.

Plasma glucose monitoring should be carried out by all patients, and insulin-treated patients should be taught to adjust their insulin doses accordingly. Glucose levels can be tested with easy-to-use home analyzers using a drop of fingertip blood. A spring-powered lancet is recommended to obtain the fingertip blood sample. The frequency of testing is determined individually. Insulin-treated diabetic patients ideally should test their plasma glucose daily before meals, 1 to 2 hours after meals, and at bedtime.

Most physicians periodically determine glycosylated hemoglobin (Hb $A_{1c}$) to estimate plasma glucose control during the preceding 1 to 3 months. Hb $A_{1c}$ is the stable product of non-enzymatic glycosylation of Hb by plasma glucose and is formed at rates that increase with increasing plasma glucose levels. In most laboratories, the normal Hb $A_{1c}$ level is about 6%; in poorly controlled diabetics, the level ranges from 9 to 12%. Hb $A_{1c}$ is not a specific test for diagnosing diabetes; however, elevated Hb $A_{1c}$ often indicates existing diabetes.

Another test determines the fructosamine level. Fructosamine is formed by a chemical reaction of glucose with plasma protein and reflects glucose control in the previous 1 to 3 weeks. Therefore, this assay may show a change in control before Hb $A_{1c}$ and is often helpful when intensive treatment is applied and in short-term clinical trials.

As regards insulin treatment, human insulin is often preferred in initiating insulin treatment because it is less antigenic than animal-derived varieties. However, detectable insulin antibody levels, usually very low, develop in most insulin-treated patients, including those receiving human insulin preparations.

Insulin is routinely provided in preparations containing 100 U/ml (U-100 insulin) and is injected subcutaneously with disposable insulin syringes. The ½-ml syringes are generally preferred by patients who routinely inject doses of <=50 U, because they can be read more easily and facilitate the accurate measurement of smaller doses. A multiple-dose insulin injection device (NovolinPen), commonly referred to as an insulin pen, is designed to use a cartridge containing several days' dosage. Insulin should be refrigerated but never frozen; however, most insulin preparations are stable at room temperature for months, which facilitates their use at work and when traveling.

Diabetes may be associated with other endocrine diseases. Type II DM can be secondary to Cushing's syndrome, acromegaly, pheochromocytoma, glucagonoma, primary aldosteronism, or somatostatinoma. Most of these disorders are associated with peripheral or hepatic insulin resistance. Many patients will become diabetic once insulin secretion is also decreased. The prevalence of type I DM is increased in patients with certain autoimmune endocrine diseases, e.g. Graves' disease, Hashimoto's thyroiditis, and idiopathic Addison's disease.

Diabetes may also be induced by beta-cell toxins. Streptozotocin for instance can induce experimental diabetes in rats but rarely causes diabetes in humans.

Late complications of diabetes occur after several years of poorly controlled hyperglycemia. Glucose levels are increased in all cells except where there is insulin-mediated glucose uptake (mainly muscle), resulting in an increase in glycolysation and in the activity of other metabolic pathways, which may be caused by complications. Most microvascular complications can be delayed, prevented, or even reversed by tight glycemic control, i.e. achieving near-normal fasting and postprandial glucose levels, reflected by near-normal glycosylated hemoglobin (Hb $A_{1c}$). Macrovascular disease such as atherosclerosis may lead to symptomatic coronary artery disease, claudication, skin breakdown, and infections. Although hyperglycemia may accelerate atherosclerosis, many years of hyperinsulinemia preceding the onset of diabetes (with insulin resistance) may play a major initiating role. Amputation of a lower limb for severe peripheral vascular disease, intermittent claudication, and gangrene remains common. Background retinopathy (the initial retinal changes seen on ophthalmoscopic examination or in retinal photographs) does not significantly alter vision, but it can progress to macular edema or proliferative retinopathy with retinal detachment or hemorrhage, which can cause blindness. About 85% of all diabetics eventually develop some degree of retinopathy. Diabetic nephropathy is usually asymptomatic until end-stage renal disease develops, but it can cause the nephrotic syndrome.

Diabetic neuropathy is a further complication of diabetes, but it is also common in connection with other diseases.

Multiple mononeuropathy is usually secondary to collagen vascular disorders (e.g. polyarteritis nodosa, systemic lupus erythematosus (SLE), Sjögren's syndrome, rheumatoid arthritis (RA)), sarcoidosis, metabolic diseases (e.g. diabetes, amyloidosis), or infectious diseases (e.g. Lyme disease, HIV infection). Microorganisms may cause multiple mononeuropathy by direct invasion of the nerve (e.g. in leprosy).

Polyneuropathy due to acute febrile diseases may result from a toxin (e.g. in diphtheria) or an autoimmune reaction (e.g. in Guillain-Barré syndrome); the polyneuropathy that sometimes follows immunizations is probably also autoimmune.

Toxic agents generally cause polyneuropathy but sometimes mononeuropathy. They include emetine, hexobarbital, barbital, chlorobutanol, sulfonamides, phenytoin, nitrofurantoin, the vinca alkaloids, heavy metals, carbon monoxide, triorthocresyl phosphate, orthodinitrophenol, many solvents, other industrial poisons, and certain AIDS drugs (e.g. zalcitabine, didanosine).

Nutritional deficiencies and metabolic disorders may result in polyneuropathy. B vitamin deficiency is often the cause (e.g. in alcoholism, beriberi, pernicious anemia, isoniazid-induced pyridoxine deficiency, malabsorption syndromes, and hyperemesis gravidarum). Polyneuropathy also occurs in hypothyroidism, porphyria, sarcoidosis, amyloidosis, and uremia.

Malignancy may cause polyneuropathy via monoclonal gammopathy (multiple myeloma, lymphoma), amyloid invasion, or nutritional deficiencies or as a paraneoplastic syndrome.

Polyneuropathy due to metabolic disorders, such as diabetes mellitus or renal failure, develops slowly, often over months or years. It frequently begins with sensory abnormalities in the lower extremities that are often more severe distally than proximally. Peripheral tingling, numbness, burning pain, or deficiencies in joint proprioception and vibratory sensation are often prominent. Pain is often worse at night and may be aggravated by touching the affected area or by temperature changes. In severe cases, there are objective signs of sensory loss, typically with stocking-and-glove distribution. Achilles and other deep tendon reflexes are diminished or absent. Painless ulcers on the digits or Charcot's joints may develop when sensory loss is profound. Sensory or proprioceptive deficits may lead to gait abnormalities. Motor involvement results in distal muscle weakness and atrophy. The autonomic nervous system may be additionally or selectively involved, leading to nocturnal diarrhea, urinary and fecal incontinence, impotence, or postural hypotension. Vasomotor symptoms vary. The skin may be paler and drier than normal, sometimes with dusky discoloration; sweating may be excessive. Trophic changes (smooth and shiny skin, pitted or ridged nails, osteoporosis) are common in severe, prolonged cases.

Treatment of the systemic disorder (e.g. diabetes mellitus, renal failure, multiple myeloma, tumor) may halt progression and improve symptoms, but recovery is slow. Entrapment neuropathies may require corticosteroid injections or surgical decompression. Physical therapy and splints reduce the likelihood or severity of contractures.

Diabetes mellitus can cause sensorimotor distal polyneuropathy (most common), multiple mononeuropathy, and focal mononeuropathy (e.g. of the oculomotor or abducens cranial nerves). Polyneuropathy commonly occurs as a distal, symmetric, predominantly sensory polyneuropathy that causes sensory deficits, which begin with and are usually marked by a stocking-glove distribution.

Generally, peripheral neuropathy is defined as a syndrome of sensory loss, muscle weakness and atrophy, decreased deep tendon reflexes, and vasomotor symptoms, alone or in any combination. The disease may affect a single nerve (mononeuropathy), two or more nerves in separate areas (multiple mononeuropathy), or many nerves simultaneously (polyneuropathy). The axon may be primarily affected (such as in diabetes mellitus, Lyme disease, or uremia or with toxic agents) or the myelin sheath or Schwann cell (such as in acute or chronic inflammatory polyneuropathy, leukodystrophies, or Guillain-Barré syndrome). Damage to small unmyelinated and myelinated fibers results primarily in loss of temperature and pain sensation; damage to large myelinated fibers results in motor or proprioceptive defects. Some neuropathies (e.g. due to lead toxicity, dapsone use, tick bite, porphyria, or Guillain-Barré syndrome) primarily affect motor fibers; others (e.g. due to dorsal root ganglionitis of cancer, leprosy, AIDS, diabetes mellitus, or chronic pyridoxine intoxication) primarily affect the dorsal root ganglia or sensory fibers, producing sensory symptoms. Occasionally, cranial nerves are also involved (e.g. in Guillain-Barré syndrome, Lyme disease, diabetes mellitus, and diphtheria).

Trauma is the most common cause of a localized injury to a single nerve. Violent muscular activity or forcible overextension of a joint may produce a focal neuropathy, as may repeated small traumas (e.g. tight gripping of small tools, excessive vibration from air hammers). Pressure or entrapment paralysis usually affects superficial nerves (ulnar, radial, peroneal) at bony prominences (e.g. during sound sleep or during anesthesia in thin or cachectic persons and often in alcoholics) or at narrow canals (e.g. in carpal tunnel syndrome). Pressure paralysis may also result from tumors, bony hyperostosis, casts, crutches, or prolonged cramped postures (e.g. in gardening). Hemorrhage into a nerve and exposure to cold or radiation may also cause neuropathy. Mononeuropathy may further result from direct tumor invasion.

Diabetic polyneuropathy may cause numbness, tingling, and paresthesias in the extremities and, less often, debilitating, severe, deep-seated pain and hyperesthesias. Ankle jerks are usually decreased or absent. Other causes of polyneuropathy must be excluded. Acute, painful mononeuropathies affecting the 3rd, 4th, or 6th cranial nerve as well as other nerves, such as the femoral, may spontaneously improve over weeks to months, occur more frequently in older diabetics, and are attributed to nerve infarctions. Autonomic neuropathy occurs primarily in diabetics with polyneuropathy and can cause postural hypotension, disordered sweating, impotence and retrograde ejaculation in men, impaired bladder function, delayed gastric emptying (sometimes with dumping syndrome), esophageal dysfunction, constipation or diarrhea, and nocturnal diarrhea. A decrease in heart rate response to the Valsalva maneuver or on standing and unchanged heart rate variation during deep breathing are evidence of autonomic neuropathy in diabetics.

Diabetic polyneuropathy is the major cause for foot ulcers and joint problems, which are important causes of morbidity in diabetes mellitus. In diabetic polyneuropathy, the sensory denervation impairs the perception of trauma from such common causes as ill-fitting shoes or pebbles. Alterations in proprioception lead to an abnormal pattern of weight bearing and sometimes to the development of Charcot's joints.

Patients with infected foot ulcers frequently feel no pain because of neuropathy and have no systemic symptoms until late in a neglected course. Deep ulcers and particularly ulcers associated with any detectable cellulitis require immediate hospitalization, since systemic toxicity and permanent disability may develop. Early surgical debridement is an essential part of management, but amputation is sometimes necessary.

Interleukin-6 (IL-6) is a multifunctional cytokine produced and secreted by several different cell types. This pleiotropic cytokine plays a central role in cell defense mechanisms including the immune response, acute phase response and hematopoiesis. IL-6 is a 20 to 26 kDa glycoprotein having 185 amino acids that has been cloned previously (May et al, (1986); Zilberstein et al, (1986); Hirano et al, (1986)). IL-6 has previously been referred to as B cell stimulatory factor 2 (BSF-2), interferon-beta 2 and hepatocyte stimulatory factor. IL-6 is secreted by a number of different tissues including the liver, spleen, and bone marrow and by a variety of cell types including monocytes, fibroblasts, endothelial, B- and T-cells. IL-6 is activated at the transcriptional level by a variety of signals including viruses, double stranded RNA, bacteria and bacterial lipopolysaccarides, and inflammatory cytokines such as IL-1 and TNF.

IL-6 has been implicated in the pathogenesis of human inflammatory CNS diseases. Increased plasma and cerebrospinal fluid levels of IL-6 have been demonstrated in patients with multiple sclerosis (Frei et al., (1991)), for instance.

Recent experiments on the effects of IL-6 on cells of the central and peripheral nervous system indicate that IL-6 may have protective effects on neuronal cells as well as some impact on inflammatory neurodegenerative processes (Gadient and Otten, 1997, Mendel et al, 1998). IL-6 was found to prevent glutamate-induced cell death in hippocampal (Yamada et al., 1994) as well as in striatal (Toulmond et al., 1992) neurons. In transgenic mice expressing high levels of both human IL-6 and human soluble IL-6R (sIL-6-R), an accelerated nerve regeneration was observed following injury of the hypoglossal nerve as shown by retrograde labeling of the hypoglossal nuclei in the brain (Hirota et al, 1996). Furthermore, there has been some evidence that IL-6 is implied in a neurological disease, the demyelinating disorder Multiple Sclerosis (MS) (Mendel et al., 1998). Mice lacking the IL-6 gene were resistant to the experimental induction of the disease. On the other hand, there have been reports indicating that IL-6 has a negative effect on neuronal survival during early post-traumatic phase after nerve injury (Fisher et al., 2001)

The biological activities of IL-6 are mediated by a membrane receptor system comprising two different proteins one named IL-6 receptor or gp80 and the other gp130 (reviewed by Hirano et al, 1994). gp130 is a transmembrane glycoprotein with a length of 918 amino acids, including an intracellular domain of 277 amino acids, is a subunit constituent of several cytokine receptors, including those for IL-6, IL-11, LIF, Oncostatin M, CNTF (ciliary neurotrophic factor), CT-1. IL-6 being the prototype of the cytokines acting through gp130, this cytokine family is also called "IL-6 type cytokines".

gp130 participates in the formation of high-affinity receptors for these cytokines by binding to low affinity receptor chains. Accordingly, gp130 has been called also an "affinity converter". Ligand binding to a cytokine receptor leads to the dimerization of gp130 (shown for the IL6 receptor) or heterodimerization (shown for LIF, Oncostatin M, and CNTF receptors) with a gp130-related protein known as the LIFR-beta subunit. Binding of the respective ligands is associated with the activation/association of a family of tyrosine kinases known as Janus kinases (JAKs), as the first step of intracellular signal transduction. Intracellular signaling processes include tyrosine phosphorylation and activation factors called STATs (signal transducer and activator of transcription).

The human gp130 gene product appears to be homologous to two distinct chromosomal loci on chromosomes 5 and 17. The presence of two distinct gp130 gene sequences is restricted to primates and is not found in other vertebrates.

It has been shown that the signaling activities of IL-6, IL-11, CNTF, Oncostatin M and LIF can be blocked specifically by different monoclonal antibodies directed against gp130. In addition to this, monoclonal antibodies, which directly activate gp130 independently of the presence of cytokines or their receptors have been found.

Other monoclonal antibodies directed against gp130 have been shown to inhibit IL-6-mediated functions. Soluble forms of gp130 (sgp130) with molecular masses of 90 and 110 Kda have been found in human serum. They can inhibit biological functions of those cytokines utilizing receptor systems with gp130 as a component.

Soluble forms of IL-6R gp80 (sIL-6R), corresponding to the extracellular domain of gp80, are natural products of the human body found as glycoproteins in blood and in urine (Novick et al, 1990, 1992). An exceptional property of sIL-6R molecules is that they act as potent agonists of IL-6 on many cell types including human cells (Taga et al, 1989; Novick et al, 1992). Even without the intracytoplasmic domain of gp80, sIL-6R is still capable of triggering the dimerization of gp130 in response to IL-6, which in turn mediates the subsequent IL-6-specific signal transduction and biological effects (Murakami et al, 1993). sIL-6R has two types of interaction with gp130 both of which are essential for the IL-6 specific biological activities (Halimi et al., 1995), and the active IL-6 receptor complex was proposed to be a hexameric structure formed by two gp130 chains, two IL-6R and two IL-6 ligands (Ward et al., 1994; Paonessa et al, 1995).

Chimeric molecules linking the soluble IL-6 receptor and IL-6 together have been described (Chebath et al., 1997, Fischer et al., 1997, WO 99/02552 and WO 97/32891). They have been designated IL-6R/IL-6 chimera and Hyper-IL-6, respectively, and will be called IL-6R/IL-6 in the following. The IL-6R/IL-6 chimera were generated by fusing the entire coding regions of the cDNAs encoding the soluble IL-6 receptor (sIL-6R) and IL-6 (Fischer et al., 1997; Chebath et al., 1997). Recombinant IL-6R/IL-6 chimera was produced in CHO cells (Chebath et al, 1997, WO99/02552). IL-6R/IL-6 chimera binds with a higher efficiency to the gp130 chain in vitro than does the mixture of IL-6 with sIL-6R (Kollet et al, 1999).

SUMMARY OF THE INVENTION

In accordance with the present invention it has been found that the administration of substances signaling through gp130 resulted in a significant beneficial effect in an established animal model of diabetic neuropathy. Exemplary substances tested were IL-6 and an IL-6R/IL-6 chimera. Both substances showed a statistically significant beneficial effect in diabetic neuropathy, as indicated by the improvement of several parameters relating to nerve vitality.

The invention therefore relates to the use of a substance signaling through gp130 for the preparation of a medicament for treatment and/or prevention of diabetic neuropathy.

The use of cells expressing substances signaling through gp130 for the manufacture of a medicament for the treatment and/or prevention of diabetic neuropathy is a further object of the present invention. Furthermore, in accordance with the present invention, vectors comprising the coding sequences for substances signaling through gp130 are used for the manufacture of a medicament for the treatment and/or prevention of diabetic neuropathy

BRIEF DESCRIPTION OF THE DRAWINGS

FIG. 6 shows the axon diameter in micrometers in the experimental animals receiving intraperitoneal administration.

FIG. 7 shows the fiber diameter in micrometers in the experimental animals receiving intraperitoneal administration.

DETAILED DESCRIPTION OF THE INVENTION

Figure 1:
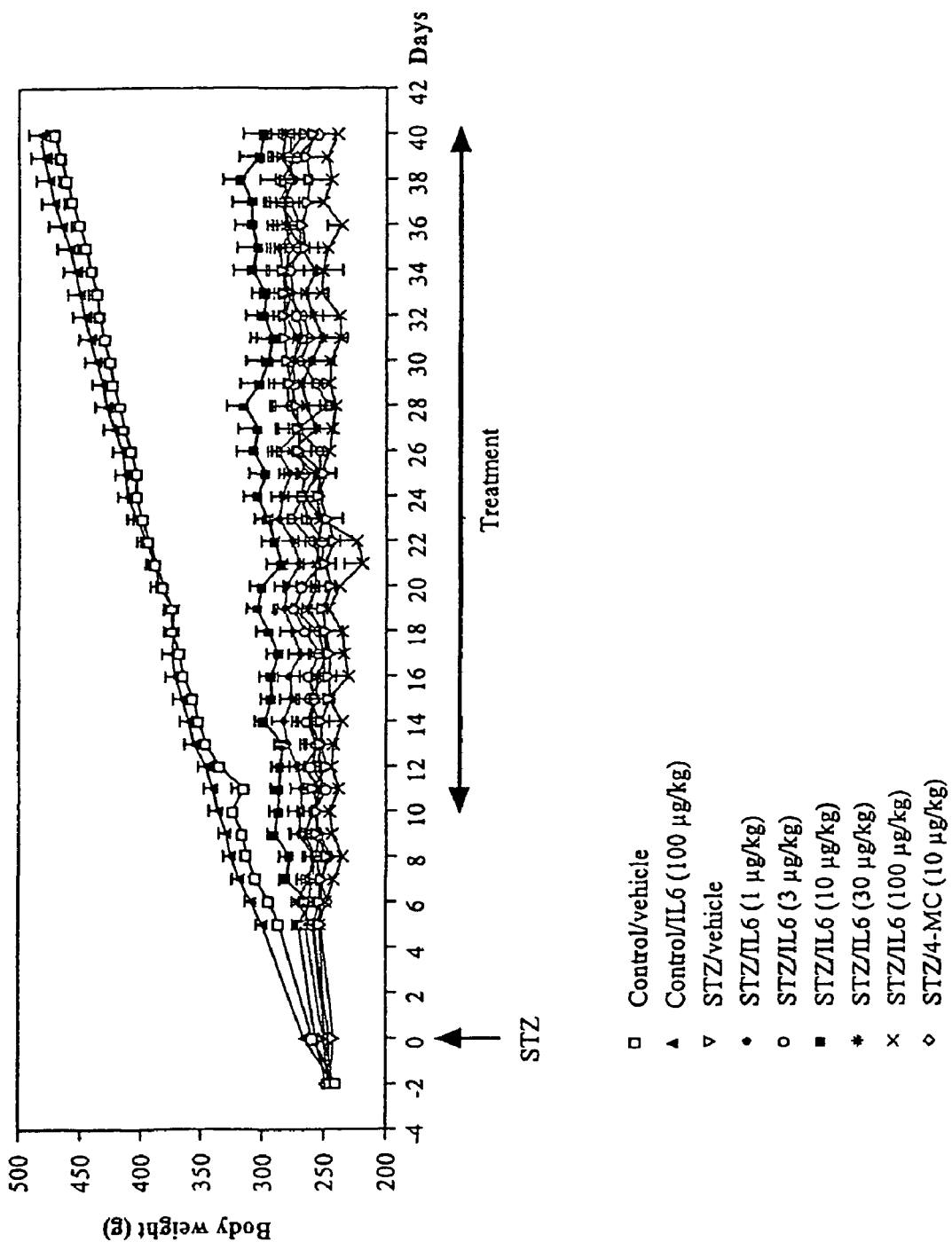
FIG. 1 shows the development of body weight in experimental animals.

The invention is based on the finding that that the administration of substances signaling through gp130 resulted in a significant antinociceptive and nerve regenerating effect in an established animal model of diabetic neuropathy. Therefore, the invention relates to the use of a substance, which initiates signaling through the human interleukin-6 (IL-6) receptor gp130 for the preparation of a medicament for treatment and/or prevention of diabetic neuropathy.

A "substance signaling through gp130" as used herein is any molecule activating the signaling cascade through gp130, i.e. any agonist, stimulator or activator of the gp130 portion of the IL-6 receptor complex. Stimulation may be direct, i.e. activation may be triggered by binding directly to gp130. An example for such a direct activator is IL-6R/IL-6 chimera. Stimulation may also be indirect by binding to another cell surface receptor, which forms a complex with gp130 thereby activating it IL-6 is an example for such an indirect activator of gp130. Further examples of substances signaling through gp130 include IL-11, LIF, Oncostatin M (OSM), CNTF (ciliary neurotrophic factor), and cardiotrophin-1 (CT-1), which are the so-called "IL-6-type cytokines". These cytokines trigger the JAK/STAT pathway, the first event of which is the ligand-induced homo- or hetero-dimerization of signal-transducing receptor subunits. All IL-6-type cytokines recruit gp130 to their receptor complexes. They either signal via gp130 alone or in combination with LIFR or OSMR, which are all able to activate Jaks and to recruit STAT proteins. IL-6 induces gp130-homodimerization, whereas CNTF, LIF, and CT-1 signal via heterodimerization of gp130 and LIFR.

The terms "treating" and "preventing" as used herein should be understood as preventing, inhibiting, attenuating, ameliorating or reversing one or more symptoms or cause(s) of diabetic neuropathy, as well as symptoms, diseases or complications accompanying diabetic neuropathy. When "treating" diabetic neuropathy, the substances according to the invention are given after onset of the disease, "prevention" relates to administration of the substances before any signs of disease can be noted in the patient. Preventive administration is especially useful in high-risk patients, such as those patients having suffered from diabetes mellitus already for a prolonged period of time.

The term "diabetic neuropathy" relates to any form of diabetic neuropathy, or to one or more symptom(s) or disorder(s) accompanying or caused by diabetic neuropathy, or complications of diabetes affecting nerves as described in detail in the introduction above.

In a preferred embodiment of the invention, the diabetic neuropathy is a polyneuropathy. In diabetic polyneuropathy, many nerves are simultaneously affected.

In a further preferred embodiment, the diabetic neuropathy is a mononeuropathy. In focal mononeuropathy, the disease affects a single nerve, such as the oculomotor or abducens cranial nerve. The disorder is called multiple mononeuropathy when two or more nerves are affected in separate areas.

Preferably, the substance is:
a) IL-6;
b) a fragment of a) which binds to gp80 and initiates signaling through gp130;
c) a variant of a) or b) which has at least 70% sequence identity with a) or b) and which initiates signaling through gp130;
d) a variant of a) or b) which is encoded by a DNA sequence which hybridizes to the complement of the native DNA sequence encoding a) or b) under moderately stringent conditions and which initiates signaling through gp130; or
e) a salt, fused protein or functional derivative of a), b), c) or d) which initiates signaling through gp130.

The use of IL-6 itself is highly preferred according to the invention. IL-6 can be native IL-6, i.e. IL-6 isolated from a natural source, or recombinantly produced IL-6. Recombinant IL-6 is particularly preferred according to the invention.

In a further preferred embodiment of the invention, the substance is
a) An IL-6R/IL-6 chimera;
b) a fragment of a) which initiates signaling through gp130;
c) a variant of a) or b) which has at least 70% sequence identity with a) or b) and initiates signaling through gp130;
d) a variant of a) or b) which is encoded by a DNA sequence which hybridizes to the complement of the DNA sequence encoding a) or b) under moderately stringent conditions and initiates signaling through gp130; or
e) a salt, fused protein or functional derivative of a), b), c) or d) which initiates signaling through gp130.

Figure 2:
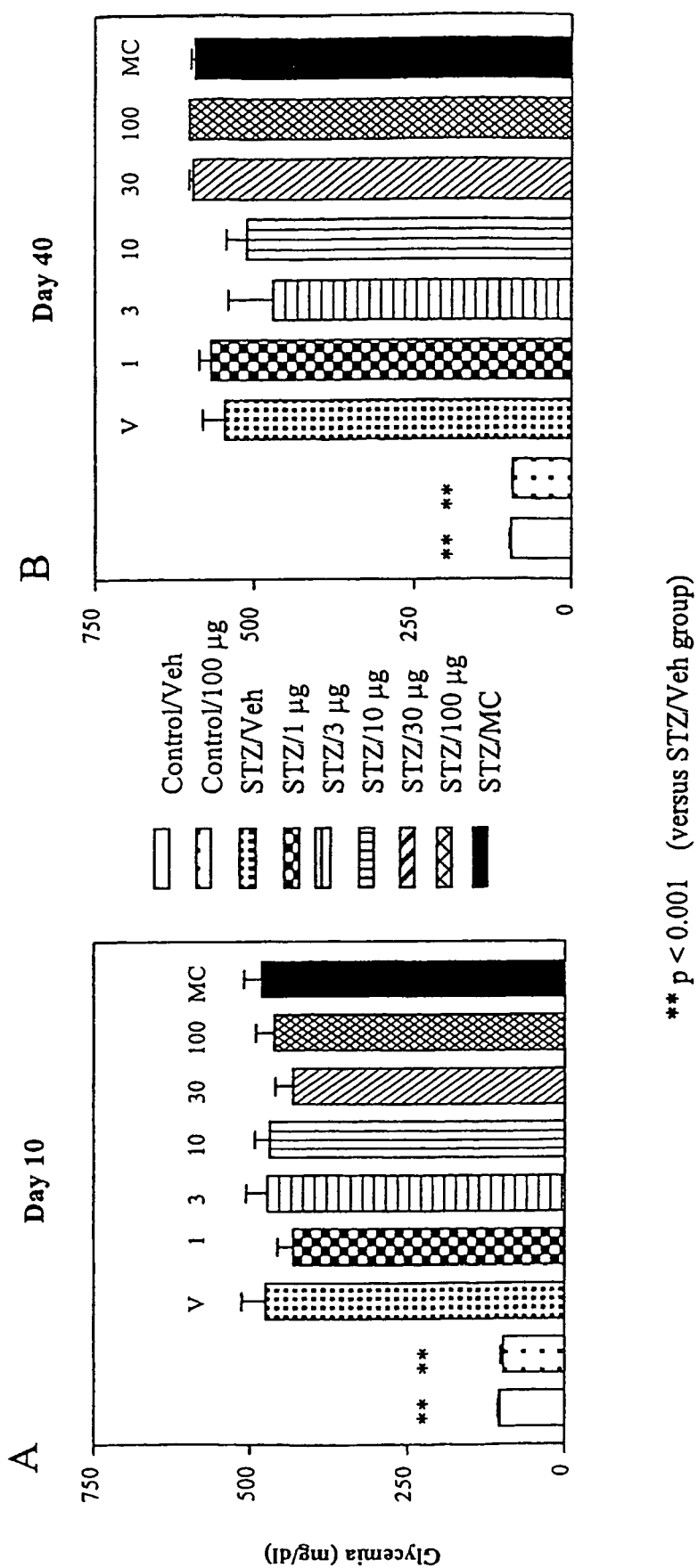
FIG. 2 shows the extent of glycemia after day 10 (A) and day 40 (B) of diabetes induction in the experimental series of animals receiving intraperitoneal administration.

An "IL-6R/IL-6 chimera" (also called "IL-6R/IL-6" or "IL-6 chimera"), as used herein, is a chimeric molecule comprising a soluble part of gp130 fused to all or a biologically active fraction of interleukin-6. The moieties of the chimeric protein can be fused directly to one another, or they can be linked by any suitable linker, such as a disulfide bridge or a polypeptide linker. The linker may be a short linker peptide which can be as short as 1 to 3 amino acid residues in length or longer, for example, 13 or 18 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the amino acid sequence of the soluble IL-6 receptor gp130 and the IL-6 sequence. Examples of IL-6R/IL-6 chimera are known in the art and have been described in detail e.g. in WO 99/02552 or WO 97/32891. An example for an IL-6R/IL-6 chimeric molecule which can be used according to the invention is depicted schematically in FIG. 2.

As used herein the term "variant" refers to analogs of IL-6 or an IL-6R/IL-6 chimera, in which one or more of the amino acid residues of the naturally occurring components of IL-6R/IL-6 are replaced by different amino acid residues, or are deleted, or one or more amino acid residues are added to the original sequence of IL-6 or an IL-6R/IL-6, without changing considerably the activity of the resulting products as compared to the original IL-6 or IL-6R/IL-6 chimera. These variants are prepared by known synthesis and/or by site-directed mutagenesis techniques, or any other known technique suitable therefor.

Variants in accordance with the present invention include proteins encoded by a nucleic acid, such as DNA or RNA, which hybridizes to the complement of the DNA or RNA encoding IL-6 or an IL-6R/IL-6 under moderately stringent or stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g. 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC, see Ausubel, supra. "Moderately stringent conditions", refer to washing conditions at lower temperatures, lower salt or lower detergent concentrations, such as in 0.2×SSC/0.1% SDS at 42° C. (Ausubel et al., 1989, supra)

Any such variant preferably has a sequence of amino acids sufficiently duplicative of that of IL-6 or an IL-6R/IL-6, such as to have substantially similar, or even better, activity as compared to IL-6 or IL-6R/IL-6.

A characteristic activity of IL-6 is its capability of binding to the gp80 portion of the IL-6 receptor, and a characteristic activity of IL-6R/IL-6 chimera is its capability of binding to gp130. An ELISA type assay for measuring the binding of IL-6R/IL-6 chimera to gp130 has been described in detail in example 7 on page 39 of WO 99/02552, which is fully incorporated by reference herein. The person skilled in the art will appreciate that a similar ELISA type assay can be developed for the binding of IL-6 to gp80. As long as the variant has substantial binding activity to its respective binding region of gp80 or of gp130, it can be considered to have substantially similar activity to IL-6 or IL-6R/IL-6 chimera. Thus, it can be determined whether any given variant has at least substantially the same activity as IL-6 or IL-6R/IL-6 by means of routine experimentation comprising subjecting such a varaint, e.g. to a simple sandwich binding assay to determine whether or not it binds to an immobilized gp80 or gp130, as described in example 7 of WO 99/02552.

In a preferred embodiment, any such variant has at least 40% identity or homology with the sequence of mature IL-6 or the IL-6R/IL-6 chimeric molecule comprised in WO 99/02552. More preferably, it has at least 50%, at least 60%, at least 70%, at least 80% or, most preferably, at least 90% identity or homology thereto.

Identity reflects a relationship between two or more polypeptide sequences or two or more nucleotide sequences, determined by comparing the sequences. In general, identity refers to an exact nucleotide to nucleotide or amino acid to amino acid correspondence of the two nucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al. 1984), for example the programs BESTFIT and GAP, may be used to determine the % identity between two nucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Variants of IL-6 or IL-6R/IL-6 chimera, which can be used in accordance with the present invention, or nucleic acid coding therefor, include a finite set of substantially corresponding sequences as substitution peptides or nucleotides which can be routinely obtained by one of ordinary skill in the art, without undue experimentation, based on the teachings and guidance presented herein.

Preferred changes for variants in accordance with the present invention are what are known as "conservative" substitutions. Conservative amino acid substitutions of IL-6 or IL-6R/IL-6 chimera may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino adds, e.g. under thirty, and preferably under ten, and do not remove or displace amino acids which are critical to a functional conformation, e.g. cysteine residues. Proteins and variants thereof produced by such deletions and/or insertions come within the purview of the present invention.

Preferably, the synonymous amino acid groups are those defined in Table 1. More preferably, the synonymous amino add groups are those defined in Table 2; and most preferably the synonymous amino acid groups are those defined in Table 3.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |

TABLE 2-continued

More Preferred Groups of Synonymous Amino Acids

| Amino Acid | Synonymous Group |
| --- | --- |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
| --- | --- |
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-6 or IL-6R/IL-6 chimera, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

Specific variants of IL-6 which are useful in connection with the present invention have been described (WO9403492A1). Furthermore, EP667872B1 describes mutant IL-6 with improved biological activity over wild type IL-6. In addition to this, EP656117B1 describes methods to isolate superagonists of IL-6. The mutants or superagonists may be used according to the invention.

The term "fused protein" refers to a polypeptide comprising IL-6 or an IL-6R/IL-6 chimera, or a variant or fragment thereof, fused with another protein, which, e.g. has an extended residence time in body fluids. IL-6 or an IL-6R/IL-6 chimera, may thus be fused to another protein, polypeptide or the like, e.g. an immunoglobulin or a fragment thereof.

"Functional derivatives" as used herein cover derivatives of IL-6 or IL-6R/IL-6 chimera, and their variants and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-6 or IL-6R/IL-6, and do not confer toxic properties on compositions containing it.

These derivatives may, for example, include polyethylene glycol side-chains, which may mask antigenic sites and extend the residence of an IL-6R/IL-6 in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

A "fragment" according to the present invention may e.g. be an active fraction of IL-6 or IL-6R/IL-6. The term fragment refers to any subset of the molecule, that is, a shorter peptide which retains the desired biological activity, i.e. which has agonistic activity of gp130. Fragments may readily be prepared by removing amino adds from either end of the IL-6 or IL-6R/IL-6 molecule and testing the resultant fragment for its properties to bind to gp80 or gp130, respectively. Proteases for removing one amino add at a time from either the N-terminal or the C terminal of a polypeptide are known in the art, and so determining fragments which retain the desired biological activity involves purely routine experimentation.

As fragments of IL-6 or an IL-6R/IL-6 chimera, variants and fused proteins thereof, the present invention further covers any fragment or precursors of the polypeptide chain of the protein molecule alone or together with associated molecules or residues linked thereto, e.g. sugar or phosphate residues, or aggregates of the protein molecule or the sugar residues by themselves, provided said fraction has agonistic activity on gp130, and in particular on gp130.

The term "salts" herein refers to both salts of carboxyl groups and to acid addition salts of amino groups of the IL-6 or an IL-6R/IL-6 molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Add addition salts include, for example, salts with mineral acids, such as, for example, hydrochloric add or sulfuric acid, and salts with organic acids, such as, for example, acetic acid or oxalic acid. Of course, any such salt must retain the biological activity of IL-6 or IL-6R/IL-6 chimera, i.e., the ability to activate signaling through gp130.

In a preferred embodiment of the invention, the substance of the invention is glycosylated at one or more sites.

A glycosylated form of an IL-6R/IL-6 chimera has been described in WO 99/02552 (PCT/IL98/00321), which is the chimeric molecule highly preferred according to the invention. The IL-6R/IL-6 chimera described therein is a recombinant glycoprotein which was obtained fusing the entire coding sequence of the naturally-occurring soluble IL-6 receptor δ-Val (Novick et al., 1990) to the entire coding sequence of mature naturally-occurring IL-6, both from human origin. The person skilled in the art will appreciate that glycosylated IL-6 can be produced by recombinant means as well, i.e. by expression in eukaryotic expression systems.

In accordance with the present invention, agonist may be produced in any adequate eukaryotic or procaryotic cell type, like yeast cells, insect cells, bacteria, and the like. It is preferably produced in mammalian cells, most preferably in genetically engineered CHO cells as described for IL-6R/

IL-6 in WO 99/02552. Whilst the protein from human origin is preferred, it will be appreciated by the person skilled in the art that a similar fusion protein of any other origin may be used according to the invention, as long as it retains the biological activity described herein.

In a further embodiment of the invention, the substance of the invention is not glycosylated. Advantageously, the chimeric molecule can then be produced in bacterial cells, which are not capable of synthesizing glycosyl residues, but usually have a high yield of produced recombinant protein. The production of nonglycosylated IL-6 has been described in detail in EP504751B1, for example.

In yet a further embodiment, the substance according to the invention comprises an immunoglobulin fusion, i.e. the molecules according to the invention are fused to all or a portion of an immunoglobulin, and in particular to an Fc fragment of an immunoglobulin. Methods for making immunoglobulin fusion proteins are well known in the art, such as the ones described in WO 01/03737, for example. The person skilled in the art will understand that the resulting fusion protein of the invention retains the biological activity of IL-6 or IL-6R/IL-6 chimera, i.e. the stimulation of gp130 signaling. The resulting fusion protein ideally has improved properties, such as an extended residence time in body fluids (half-life), increased specific activity, increased expression level, or facilitated purification of the fusion protein.

Preferably, the substance of the invention is fused to the constant region of an Ig molecule. It may be fused to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may thus be monomeric or multimeric, hetero- or homomultimeric.

Functional derivatives of the substance of the invention may be conjugated to polymers in order to improve the properties of the protein, such as the stability, half-life, bioavailability, tolerance by the human body, or immunogenicity.

Therefore, a preferred embodiment of the invention relates to a functional derivative of the substance of the invention comprising at least one moiety attached to one or more functional groups which occur as one or more side chains on the amino acid residues.

A highly preferred embodiment relates to a substance of the invention linked to Polyethlyeneglycol (PEG). PEGylation may be carried out by known methods, such as the ones described in WO 92/13095, for example.

Preferably, the substance signaling through gp130 is used in an amount ranging from about 0.1 to 1000 µg/kg or about 1 to 500 µg/kg or less than about 100 µg/kg. It is further preferred to use the substance signaling through gp130 in an amount of about 1 µg/kg or 3 µg/kg or 10 µg/kg or 30 µg/kg.

In a preferred embodiment of the invention, the substance signaling through gp130 is administered daily. In a further preferred embodiment, the substance signaling through gp130 is administered three times per week. In yet a further preferred embodiment, the substance signaling through gp130 is administered once a week.

The substance of the invention may be administered by any adequate route. The subcutaneous route is highly preferred in accordance with the present invention.

The substance of the invention may be delivered to its site of action in any adequate formulation. Preferably, it may be delivered in form of cells expressing and/or secreting IL-6, IL-6R/IL-6 chimera, a variant, fused protein or active fraction thereof. As illustrated in the examples below, cells expressing and secreting IL-6R/IL-6 chimera in sufficient amounts have been generated by transfection into the cells using a suitable expression vector.

The invention therefore further relates to the use of a cell expressing a substance according to the invention, for manufacture of a medicament for the treatment and/or prevention of diabetic neuropathy. The cells may be administered in any suitable form. However, a polymer-encapsulated IL-6 or an IL-6R/IL-6 chimera expressing, and preferably secreting cell, is a highly preferred mode of delivery of IL-6R/IL-6 chimera. The encapsulation procedure is described in detail e.g. by Emerich et al (1994) or U.S. Pat. No. 5,853,385. Suitable cell lines and stable expression systems are well known in the art.

The delivery of the substance according to the invention may also be carried out using a vector, such as an expression vector, comprising the coding sequence of IL-6, an IL-6R/IL-6 chimera, a variant, fused protein or fragment thereof. The vector comprises all regulatory sequences needed for expression of the desired protein in the human body, and preferably in peripheral nervous cells. Regulatory sequences for expression vectors are known by the person skilled in the art. The invention thus also relates to the use of a vector comprising the coding sequence of a substance according to the invention for manufacture of a medicament for the treatment and/or prevention of diabetic neuropathy.

Any expression vector known in the art may be used according to the invention. However, the use of a virally derived gene therapy vector is highly preferred.

The substance of the invention is preferably administered to the human body as a pharmaceutical composition. The pharmaceutical composition may comprise the polypeptide of the invention as such, or cell expressing said polypeptide, or an expression vector, in particular a lentiviral gene therapy vector comprising the coding sequence of IL-6, an IL-6R/IL-6 chimera or a variant, fused protein, or active fragment thereof, optionally together with one or more pharmaceutically acceptable carriers, diluents or excipients, for the treatment and/or prevention of diabetic neuropathy.

The definition of "pharmaceutically acceptable" is meant to encompass any carrier, which does not interfere with effectiveness of the biological activity of the active ingredient and that is not toxic to the host to which it is administered. For example, for parenteral administration, the active component may be formulated in a unit dosage form for injection in vehicles such as saline, dextrose solution, serum albumin and Ringer's solution.

The active component can be administered to a patient in a variety of ways. The routes of administration include intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule is administered to the patient (e.g. via a vector) which causes the active polypeptide to be expressed and secreted in vivo. In addition the active molecule can be administered together with other components of biologically active agents such as pharmaceutically acceptable surfactants, excipients, carriers, diluents and vehicles.

For parenteral (e.g. intravenous, subcutaneous, intramuscular) administration, the active component can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

It is a further object of the present invention to provide for a method for treating and/or preventing diabetic neuropathy, comprising administering to a patient in need thereof an effective amount of a substance which initiates signaling through the human gp130 receptor, optionally together with a pharmaceutically acceptable carrier.

An "effective amount" refers to an amount of the active ingredients that is sufficient to affect the course and the severity of the diseases described above, leading to the reduction or remission of such pathology. The effective amount will depend on the route of administration and the condition of the patient.

The dosage administered, as single or multiple doses, to an individual will vary depending upon a variety of factor, including pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

A method for treating diabetic neuropathy, comprising administering to a patient in need thereof an effective amount of a cell expressing IL-6 or an IL-6R/IL-6 chimera, or a variant, fused protein, active fraction thereof, is also considered in accordance with the present invention. A method for treating diabetic neuropathy comprising administering to a patient in need thereof an expression vector comprising the coding sequence of IL-6 or an IL-6R/IL-6 chimera, a variant, fused protein, or active fraction thereof, is a further objects of the invention.

In a preferred embodiment of the invention, the expression vector is a gene therapy vector. The use of a viral vector, in particular a lentiviral vector, is highly preferred.

The present invention will now be described in more detail in the following non-limiting examples and the accompanying drawings.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Production of IL-6 and IL-6R/IL-6 Chimera in CHO Cells

IL-6R/IL-6 Chimera

The cDNA sequences encoding for the soluble IL-6 receptor (natural form of sIL-6R found in urine, Oh et al., 1997) have been fused with those encoding for mature IL-6. Sequences for 3 bridging amino acids (EFM) were also present. The fused gene was inserted in an expression vector under the control of CMV promoter and introduced into CHO cells. A production process has been developed and the resulting recombinant protein has been purified by immunopurification using an anti-IL-6R monoclonal antibody. The purified IL-6 chimera has been shown to be glycosylated and to display an apparent MW of 85'000.

Figure 10:
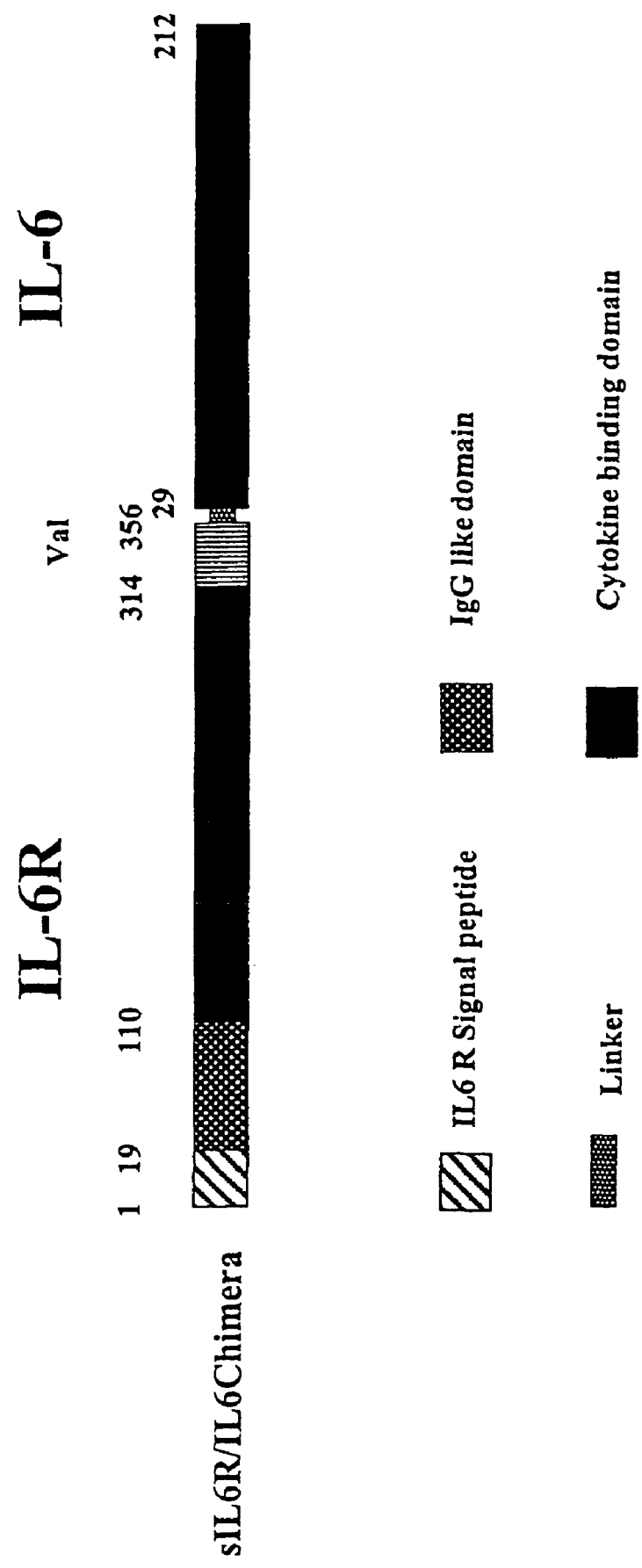
FIG. 10 is a schematic drawing illustrating the IL-6R/IL-6 chimera structure.

FIG. 10 schematically shows the composition of the IL-6R/IL-6 chimera. The mature protein comprises 524 amino acids.

A protein produced and purified as outlined above is suitable to be administered according to the invention.

IL-6

Recombinant human IL-6 (r-hIL-6) is produced in genetically engineered Chinese Hamster Ovary (CHO) cells. The production process begins with the growth and expansion of cells from a working cell bank (WCB) and continues under conditions where r-hIL-6 is secreted into the culture medium. The r-hIL-6 harvested culture medium is purified by immunochromatography using a specific anti-IL-6 monoclonal antibody (mAB). Further purification steps are used to yield a product with a very high level of purity.

r-hIL-6 is supplied as a sterile, freeze-dried preparation containing suitable excipients. It is available in 2 different amounts, 35 µg and 350 µg, and is reconstituted for use with water for injection. The reconstitution volume for one vial of final formulated product is normally 0.5 ml of water. The finished product should be stored in its original container at a temperature below 25° C.

The structure of r-hIL-6 has been confirmed by fast atomic bombardment mass spectroscopy (FAB-MS), tryptic mapping and amino acid sequencing. FAB and electrospray mass spectroscopies were used to determine the composition and FAB and electrospray mass spectroscopies were used to determine the composition and structure of the carbohydrate moieties of IL-6. Residue aspargine-46 was identified as the N glycosylation site and preliminary analysis of the N-linked carbohydrate showed that the dominant species were monosialyl fucosyl biantennary and disialyl fucosyl biantennary structures. The O-glycosylation site was identified as either threonine −138 or −139.

Example 2

Effect of IL-6 in the Streptozotozin-Induced Diabetic Neuropathy Model Upon Intraperitoneal Administration Materials and Methods Animals Six week-old male Sprague Dawley rats (Janvier, Le Genest-St-Isle, France) were distributed in 9 experimental groups (n=10) in accordance with a randomization table: (a) a vehicle control group, injected with a sterile solution of saline—BSA 0.02% (weight/volume); (b) a control group consisting of animals injected with IL-6 at a dose of 100 μg/kg dissolved in a sterile solution of saline—BSA 0.02%; (c) a streptozotocin (STZ)-intoxicated group injected with a sterile solution of saline—BSA 0.02%; (d) 5 treated, STZ-intoxicated groups consisting of animals receiving injections of IL-6 compound at 5 different doses: 1, 3, 10, 30 and 100 μg/kg; (e) a STZ-intoxicated group and treated with a reference compound: 4-methyl catechol (4-MC) at the dose of 10 μg/kg.

They were group-housed (2 animals per cage) and maintained in a room with controlled temperature (21-22° C.) and a reversed light-dark cycle (12 h/12 h) with food and water available ad libitum. All experiments were carried out in accordance with institutional guidelines.

Induction of Diabetes and Pharmacological Treatment

Diabetes was induced by injection of a buffered solution of streptozotocin (Sigma, L'Isle d'Abeau Chesnes, France) in the surgically denuded left saphena magna, at a dose of 55 mg/kg body weight. The drug was dissolved immediately before injection in 0.1 mol/l citrate buffer pH 4.5. The day of STZ injection was considered as Day (D) 0.

One week later, at D 10, tail vein blood was assayed for glycemia in each individual animal using a glucometer (Glucotrend test, Roche, Mannheim, Germany). Animals showing a value below 260 mg/dl were excluded from the study. Glycemia was checked again at D 40, at the end of the experiment.

IP treatment (vehicle, IL-6 and 4-MC) was performed daily from D 11 to D 40.

Planning of Experiments

Body weight and survival rate were recorded every day.

Tail flick and EMG testings were performed once a week as following timing:

D-7: baseline (tail flick and EMG)
D 0: induction of diabetes by STZ injection
D 10: measure of glycemia
D 11: onset of the treatment (IL-6 and 4-MC)
D 25: EMG and tail flick testing
D 40: control of glycemia, EMG and tail flick tests, removal of sciatic nerve Sensitivity Test: Tail Flick The tail of the rat was placed under a shutter-controlled lamp as a heat source (Bioseb, Paris, France). The latency before the rat flicked its tail from the heat was recorded. A sensory alteration increases the latency of flick. Two trials were performed and the mean value was calculated and retained as characteristic value.

Electromyography

Electrophysiological recordings were performed using a Neuromatic 2000M electromyograph (EMG) (Dantec, Les Ulis, France). Rats were anaesthetized by intraperitoneal injection of 60 mg/kg ketamine chlorhydrate (Imalgene 500®, Rhône Mérieux, Lyon, France). The normal body temperature was maintained at 30° C. with a heating lamp and controlled by a contact thermometer (Quick, Bioblock Scientific, Illkirch, France) placed on the tail surface.

Compound muscle action potential (CMAP) was recorded in the gastrocnemius muscle after stimulation of the sciatic nerve. A reference electrode and an active needle were placed in the hindpaw. A ground needle was inserted on the lower back of the rat. Sciatic nerve was stimulated with a single 0.2 ms pulse at a supramaximal intensity. The velocity of the motor wave was recorded and expressed in ms.

Sensitive nerve conduction velocity (SNCV) was also recorded. The tail skin electrodes were placed as follows: a reference needle inserted at the base of the tail and an anoe needle placed 30 mm away from the reference needle towards the extremity of the tail. A ground needle electrode was inserted between the anode and reference needles. The caudal nerve was stimulated with a series of 20 pulses (for 0.2 ms) at an intensity of 12.8 mA. The velocity was expressed in m/s.

Morphometric Analysis

Morphometric analysis was performed at the end of the study (D 40). The animals were anesthetized by IP injection of 100 mg/kg Imalgène 500®. A 5 mm-segment of sciatic nerve was excised for histology. The tissue was fixed overnight with 4% glutaraldehyde (Sigma, L'Isle d'Abeau-Chesnes, France) solution in phosphate buffer solution (pH=7.4) and maintained in 30% sucrose at +4° C. until use. The nerve sample was fixed in 2% osmium tetroxide (Sigma, L'Isle d'Abeau-Chesnes, France) solution in phosphate buffer solution for 2 h., dehydrated in serial alcohol solution, and embedded in Epon. Embedded tissues were then placed at +70° C. during 3 days of polymerization. Transverse sections of 1.5 μm were cut with a microtome, stained with a 1% toluidine blue solution (Sigma, L'Isle d'Abeau-Chesnes, France) for 2 min, dehydrated and mounted in Eukitt. Twenty sections per sample were examined using an optical microscope (Nikon, Tokyo, Japan) and 6 randomly selected slices were analyzed using a semi-automated digital image analysis software (Biocom, France). Two randomly selected fields per slice were studied. The following parameters were calculated: (a) fiber diameter, (b) axon diameter, (c) myelin thickness (see below).

For counting the total number of fibers per nerve section, 3 randomized slices per sample were selected and 2 fields per slice were analyzed.

Data Analysis

Global analysis of the data was performed using one factor or repeated measure analysis of variance (ANOVA) and one way ANOVA Dunnett's test was used when anova test indicated a significant difference. No post-hoc analyses were performed. The level of significance was set at $p<0.05$. Results are expressed as mean±standard error of the mean (s.e.m.).

Results

Animal Weight

As illustrated in FIG. 1, a significant intergroup difference in body weight evolution was noted in this study [$f(8, 296) =19.47$ and $p<0.001$; repeated measure ANOVA]. From d 5 to d 40, the STZ-intoxicated/IL-6-treated animals displayed a significant decrease in body weight ($p<0.05$; one way ANOVA and $p<0.05$ control versus (vs) STZ; control/il-6 (100 μg/kg) vs STZ; control vs STZ+il-6 and control/il-6 (100 μg/kg) vs STZ+IL-6; Dunnett's test).

Diabetic animals treated with IL-6 at a dose of 10 µg/kg displayed a body weight significantly higher than that of other doses of il-6 [f (5, 185)=1.16 and p=0.08; repeated measures ANOVA].

It could be noted that the STZ-intoxicated/IL-6 treated animals at the dose of 100 µg/kg displayed a body weight decreased throughout the study (starting at the beginning of the treatment).

Glycemia

FIG. 2a shows that at d 10 control animals presented a glycemia value equal at 100 mg/dl. On the other hand, STZ-intoxicated rats displayed a plasma glucose concentration higher than 260 mg/dl and were considered as diabetic.

FIG. 2b shows that STZ-intoxicated rats were still diabetic at d 40.

Sensitivity Test: Tail Flick

Figure 3:
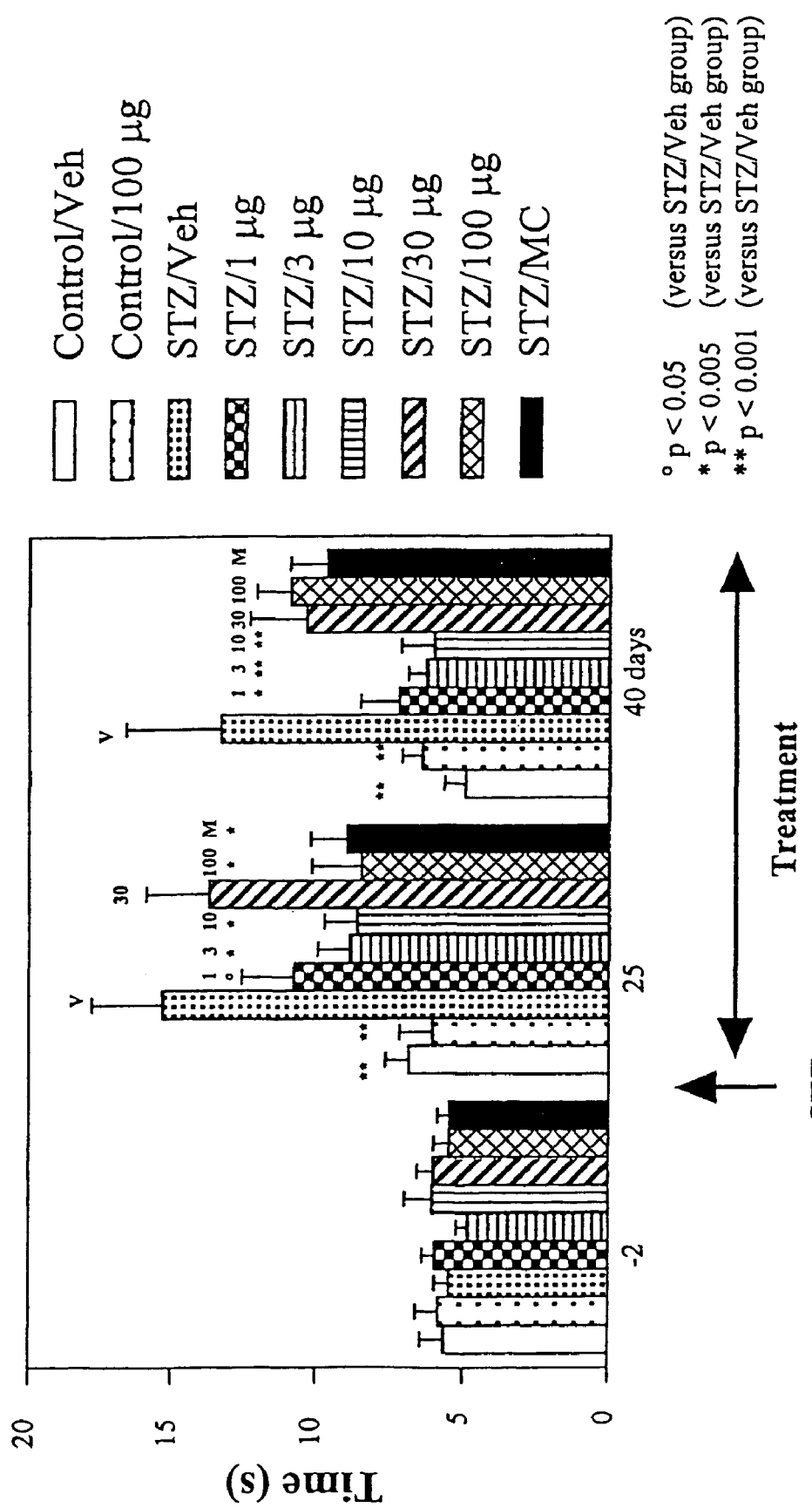
FIG. 3 shows the time taken by animals receiving intraperitoneal administration to flick their tail placed on a heat source in seconds.

There was a significant intergroup difference in the evolution of tail-flick test performances [F (8, 16)=2.07 and p=0.013; repeated measure ANOVA] (FIG. 3). The latency before the rats flicked their tail from the heat was significantly increased in diabetic non treated animals (control/vehicle vs STZ/vehicle p<0.001; Dunnett's test). In the D 25 and D 40, the reaction time was not increased in the animals treated with IL-6 at doses of 1, 3, 10 and 100 µg/kg and treated with 4-MC at 10 µg/kg. Indeed, no significant difference between these groups was found (p>0.05; Dunnett's test).

Electrophysiological Measurements

Latency of the Compound Muscle Action Potential

Figure 4:
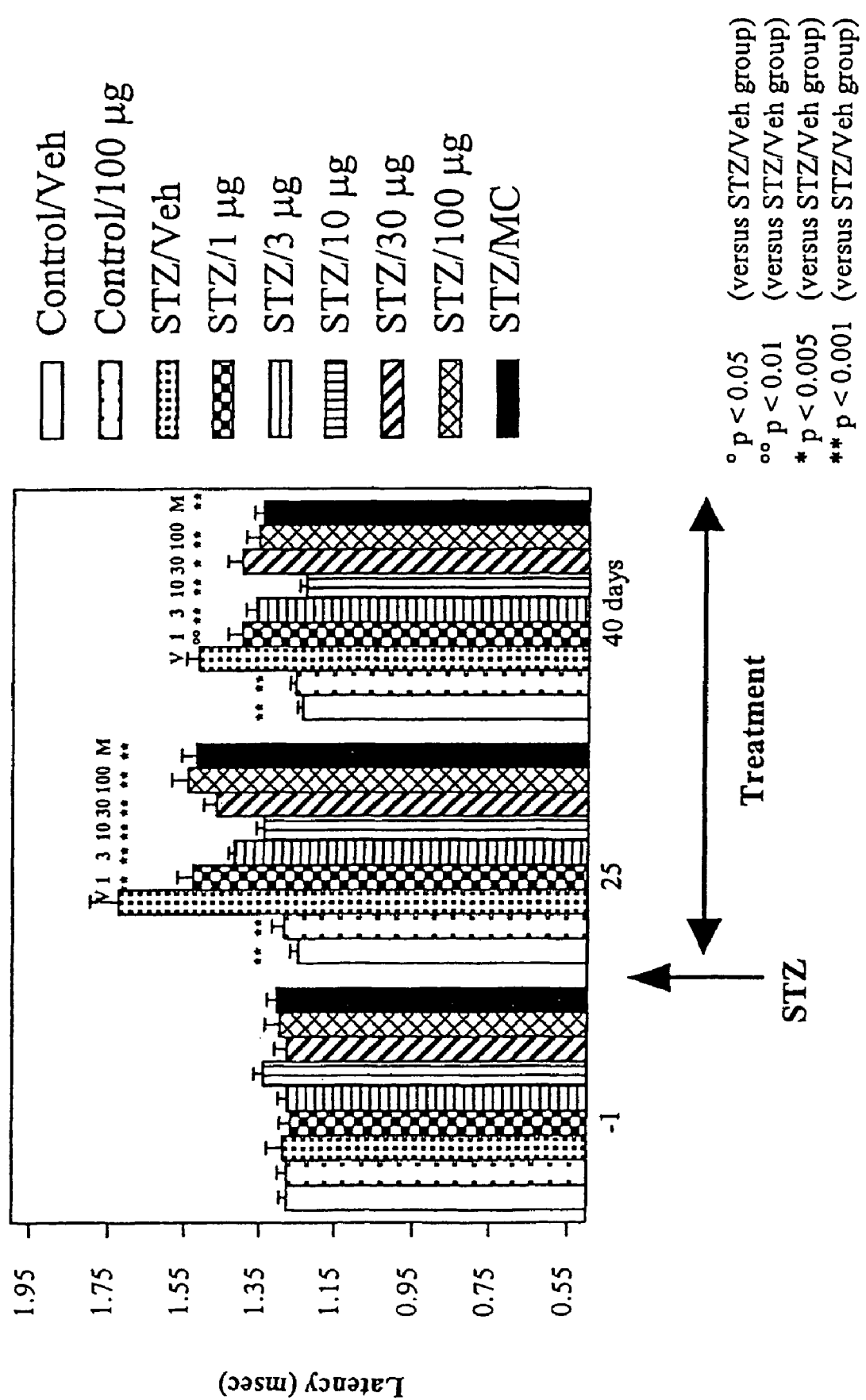
FIG. 4 shows the compound muscle action potential (CMAP) of the animals receiving intraperitoneal administration expressed in latency per second.

There was a significant difference between the groups in the latency of the CMAP throughout the study [F (8, 16)=5.901 and p<0.001; repeated measures ANOVA]. The latency was significantly increased in diabetic untreated rats (on days 25 and 40: p<0.001; one way ANOVA). This increase was less important in IL-6-treated groups; especially for the IL-6 (10 µg/kg)-treated group which presented, on days 25 and 40, no significant difference with the latency value of the control/vehicle group (FIG. 4).

Moreover, on day 25, each IL-6 treated/STZ groups displayed a CMAP latency significantly shorter than the CMAP latency of the vehicle/STZ group (p=0.001, Dunnett's test).

On day 40, the same conclusion was drawn.

A significant difference was seen between IL-6 treated/STZ animals (10 mg/kg) and the 4 other IL-6 treated groups (1, 3, 10, 30 and 100 µg/kg) (D 25: p=0.002, D 40: p=0.003; one way ANOVA test). The 3 µg/kg and 10 µg/kg treated animals displayed a lower significantly latency than the 1, 30 and 100 µg/kg IL-6 treated/STZ groups (p<0.05; Dunnett's test) on day 25 as well as day 40.

Sensory Nerve Conduction Velocity

Figure 5:
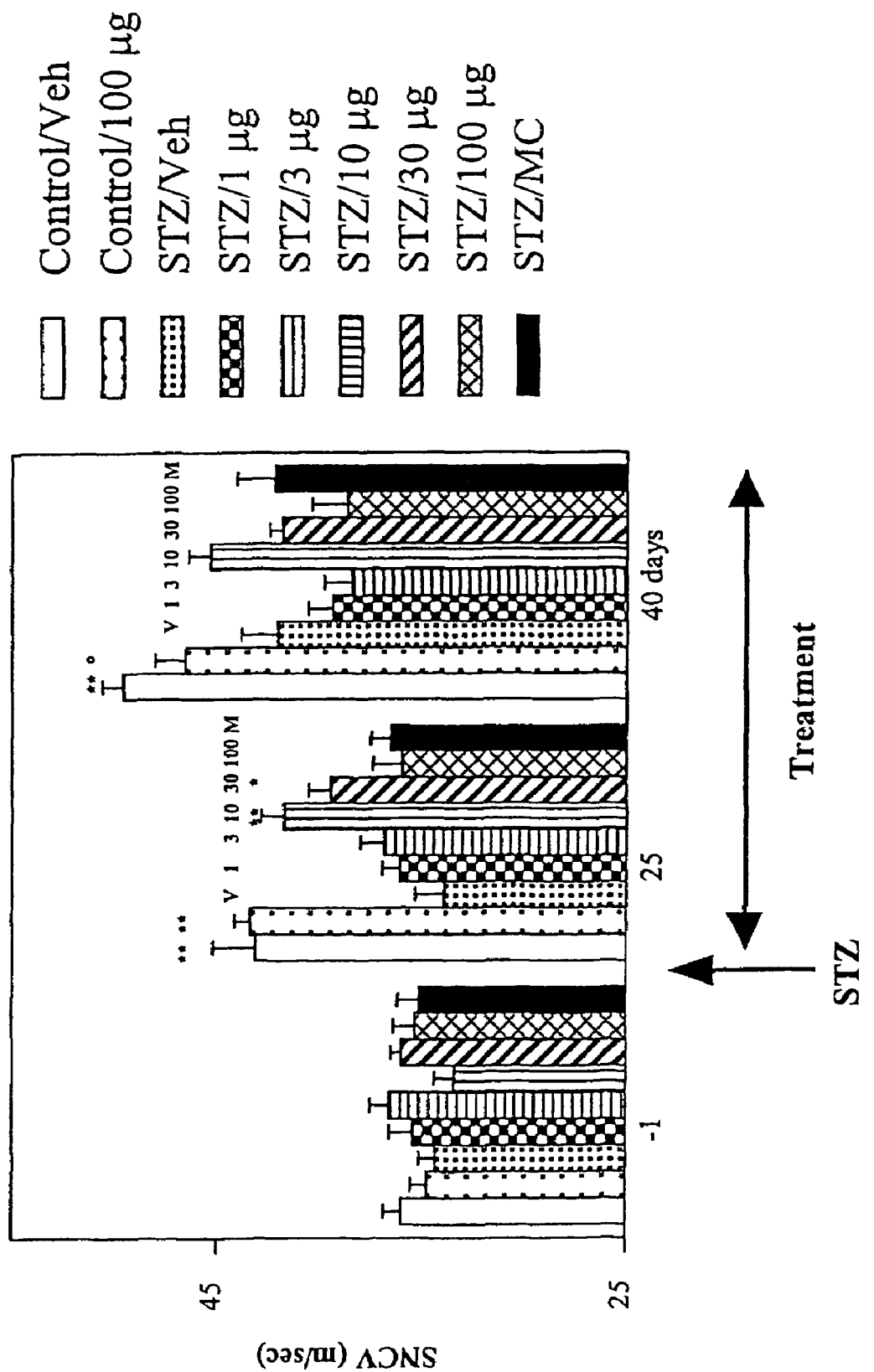
FIG. 5 shows the sensory nerve conduction velocity (SNVC) in m/sec in the experimental animals receiving intraperitoneal administration.

A significant difference was noted between the groups in the SNCV throughout the study [F (8,16)=5.518 and p<0.001; repeated measures ANOVA] (FIG. 5). Diabetic rats displayed a significant decrease of the SNCV (on days 25 and 40: p<0.001; one way ANOVA) in contrast with the control/vehicle group. Moreover, on day 25 no significant difference was observed between the control/vehicle group and the 10 µg/kg IL-6-treated group (p=0.426; Dunnett's test), whereas a significant difference was seen between all the other groups. On day 25, only the 10 and the 30 µg/kg displayed a significant difference with the STZ/vehicle group (10 µg/kg vs vehicle STZ groups: p<0.001, 30 µg/ml vs STZ groups, p=0.004, Dunnett's test). On day 40, the animal treated with 10 µg/kg did not show any significant difference with the STZ/vehicle treated animals however, the SNCV value for this group was higher than the other STZ/IL-6 treated animals.

It could be noted that the SNCV gradually increased throughout the study in the control/vehicle animals due to a normal maturation of the peripheral nerve structure (Gao et al., 1995, Malone et al., 1996).

Morphometric Analysis

Axon Diameter

A significant intergroup difference was found in the axon diameter (p<0.001; one way ANOVA) (FIG. 6). Vehicle/STZ animals displayed a significant decrease in the axon diameter in comparison with the control rats (p=0.08; Dunnett's test). Treatment with IL-6 reversed this decrease of axon diameter, since the dose of 3 µg/kg (IL-6-treated rats vs STZ/vehicle p<0.001; Dunnett's test). Moreover, a significant difference was noted between the control group and the control/IL-6 (100 µg/kg) group (p<0.001; Dunnett's test). No significant difference was found between the control/vehicle group and the 4-MC-treated group (p=0.657; Dunnett's test).

Fiber Diameter

FIG. 7 shows that there was a significant difference between the 9 groups in fiber diameter (p<0.001, one way ANOVA). The STZ administration leads to a significant decrease of fiber diameter (control/vehicle vs STZ/vehicle p=0.005; Dunnett's test). A significant difference was observed between vehicle/STZ rats and IL-6-treated/STZ rats (p<0.005; Dunnett's test). The IL-6-treated animals displayed a larger fiber diameter than vehicle/STZ animals. Moreover, a significant difference was found between the control group and the control/IL-6 (100 µg/kg) group (p<0.001; Dunnett's test). The animals treated with 4-MC at the dose of 10 µg/kg presented no significant difference with the control/vehicle group (p=0.628; Dunnett's test).

Myelin Thickness

Figure 8:
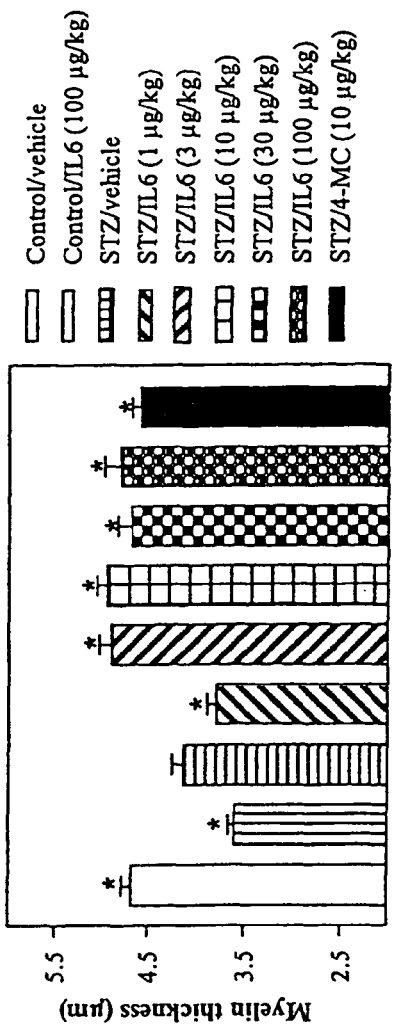
FIG. 8 shows the myelin thickness in micrometers in the experimental animals receiving intraperitoneal administration.

Comparison of the myelin thickness revealed a significant difference between the 9 groups (p<0.001; one way ANOVA) (FIG. 8). The myelin thickness was significantly smaller in vehicle/STZ animals than control/vehicle and IL-6-treated animals (3, 10, 30 and 100 µg/kg) (p<0.01; Dunnett's test). It could be noted that all the IL-6 treated/STZ animals presented a myelin thickness significantly higher than the vehicle/STZ group. Moreover, we noted a significant difference between control/vehicle and control/IL-6 (100 µg/kg) groups (p<0.001; Dunnett's test).

Total Number of Myelinated Fibers

Figure 9:
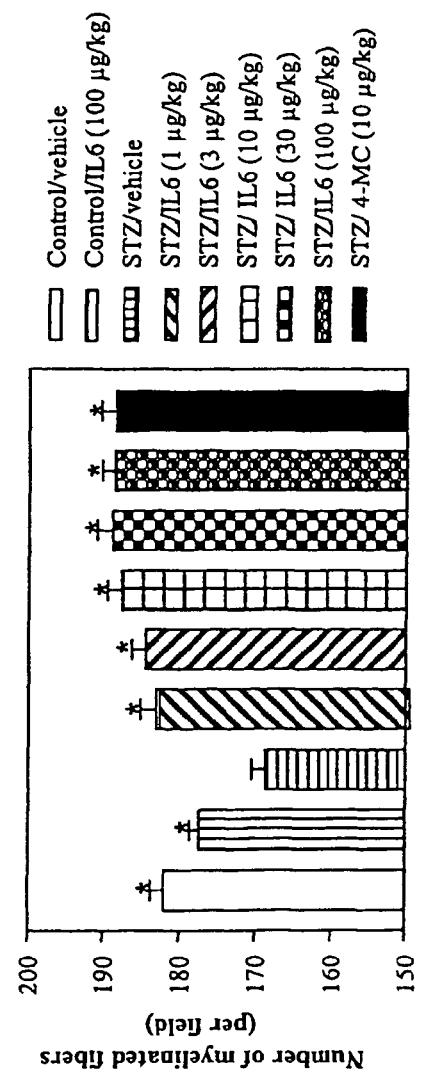
FIG. 9 shows the number of myelinated fibers per field in the experimental animals receiving intraperitoneal administration.

As shown in FIG. 9, there was a significant intergroup difference in total number of myelinated fibers (p<0.001; one way ANOVA). The vehicle/STZ animals displayed a smaller number of fibers than the control animals (p<0.001; Dunnett's test). By contrast, the IL-6-treated/STZ animals had an increased number of fibers as compared with the vehicle/STZ animals (p<0.001; Dunnett's test). The STZ-intoxicated animals treated with 4-MC had a total number of fibers analogous to those of the control animals. Moreover, no significant difference between control/vehicle group and control/IL-6 (100 µg/kg) group was noted.

CONCLUSION

In this study, animals intoxicated with the streptozotocin and which develop a diabetes several days later, have been used as model of induced-neuropathy. The animal becomes diabetic 3-4 days after the induction.

The diabetic animals have been treated by different doses of IL-6 (1, 3, 10, 30 and 100 µg/kg) on 30 days chronically. The treatment has been administrated intraperitoneally every day starting 10 days after the induction until the sacrifice of the animal 40 days after the STZ-induction. This treatment could be considered as a curative treatment in that IL-6 has been administered after the first molecular damages caused by a prolonged hyperglycemia.

The present protocol shows that a IL-6 treatment of 30 days induces a neuroprotection against the diabetic neuropathy. The behavioral analyses with tail flick and the EMG testing (sensory and motor velocities) show the neuroprotective effect of IL-6 especially for the doses of 3 and 10 μg/kg.

The low doses as well as the high concentrations displayed neuroprotective effect. Indeed, the more the doses of treatment increase, the less the neuroprotective effect is significant. Moreover, the highest dose (100 μg/kg) does not display a pronounced effect and seems to have a toxic effect on the general behavior of the STZ-animals. The control animals (not treated with STZ) treated with IL-6 at 100 μg/kg were more excited than the vehicle control animals or the STZ rats treated with low concentrations of IL-6. Moreover, these animals (IL-6 100 μg/kg) were difficult to manipulate for the experimentator. The same was observed in the STZ/IL-6 100 μg/kg. Nevertheless, these animals seemed less excited (probably due to their weakness due to their large loss of body weight).

The neuroprotective effect is focused on the sensory fibers as well as motor fibers (the CMAP velocity was not altered with a IL-6 treatment).

Concerning the morphological analysis, the neuroprotection induced by the IL-6 treatment is very clear for all studied doses. The fibers of the STZ/vehicle animals displayed a decrease of the myelin sheath and an alteration of the axon, which finally induce a degeneration of the fibers (shown with a decrease of the total number of fibers).

It was demonstrated in this study that the treatment with IL-6 (especially 10 μg/kg) protected the myelin sheath and the axonal degeneration.

It must be noted that the high dose of IL-6 (100 μg/kg) induces an harmful effect on the fibers in healthy animals. Indeed, the fibers seem to suffer, there is no loss of fiber but the sheath and the general aspect of the fibers are altered. Whereas this effect is not recorded in the diabetic animals treated with this large dose of IL-6 (the toxic effect is mainly focused on the general behavior of the animal characterized by a large decrease of the body weight).

In conclusion, IL-6 induces a dear neuroprotective effect after a chronic treatment of 30 days as well as on sensory than motor fibers, probably acting by a direct effect on the fiber and reducing the inflammatory process of neurodegeneration.

Example 3

Effect of IL-6 in the Streptozotozin-Induced Diabetic Neuropathy Model Upon Subcutaneous Administration The aim of this study was to evaluate the effect of the IL-6 via the subcutaneous route at different dosage and timing in the same model of neuropathy.

Animals

Study A

Six week-old male Sprague Dawley rats (Janvier, Le Genest-St-Isle, France) were distributed in 6 experimental groups in accordance with a randomization table: (a) a vehicle control group (n=4), injected with a sterile solution of saline—BSA 0.02% (weight/volume); (b) a streptozotocin (STZ)-intoxicated group (n=10) injected with a sterile solution of saline—BSA 0.02%; (c) 4 treated, STZ-intoxicated groups (n=10) consisting of animals receiving daily SC injections of IL-6 compound at 4 different doses: 1, 3, 10, 30 μg/kg.

They were group-housed (2 animals per cage) and maintained in a room with controlled temperature (21-22° C.) and a reversed light-dark cycle (12 h/12 h) with food and water available ad libitum. All experiments were carried out in accordance with institutional guidelines.

Study B

Six week-old male Sprague Dawley rats (Janvier, Le Genest-St-Isle, France) were distributed in 7 experimental groups in accordance with a randomization table: (a) a vehicle control group (n=4), injected with a sterile solution of saline—BSA 0.02% (weight/volume); (b) a streptozotocin (STZ)-intoxicated group (n=10) injected with a sterile solution of saline—BSA 0.02%; (c) 4 treated, STZ-intoxicated groups (n=10) consisting of animals receiving SC injections of IL-6 compound 3 times per week at 4 different doses: 1, 3, 10, 30 μg/kg; (d) a treated, STZ-intoxicated group (n=10) consisting of animals receiving IP injections of IL-6 compound at 10 μg/kg.

They were group-housed (2 animals per cage) and maintained in a room with controlled temperature (21-22° C.) and a reversed light-dark cycle (12 h/12 h) with food and water available ad libitum. All experiments were carried out in accordance with institutional guidelines.

Study C

Six week-old male Sprague Dawley rats (Janvier, Le Genest-St-Isle, France) were distributed in 6 experimental groups in accordance with a randomization table: (a) a vehicle control group (n=4), injected with a sterile solution of saline—BSA 0.02% (weight/volume); (b) a streptozotocin (STZ)-intoxicated group (n=10) injected with a sterile solution of saline—BSA 0.02%; (c) 4 treated, STZ-intoxicated groups (n=10) consisting of animals receiving SC injections of IL-6 compound once a week at 4 different doses: 1, 3, 10, 30 μg/kg.

They were group-housed (2 animals per cage) and maintained in a room with controlled temperature (21-22° C.) and a reversed light-dark cycle (12 h/12 h) with food and water available ad libitum. All experiments were carried out in accordance with institutional guidelines.

Induction of Diabetes and Pharmacological Treatment

Diabetes was induced by injection of a buffered solution of streptozotocin (Sigma, L'Isle d'Abeau Chesnes, France) in the surgically denuded left saphena magna, at a dose of 55 mg/kg body weight. The drug was dissolved immediately before injection in 0.1 mol/l citrate buffer pH 4.5. The day of STZ injection was considered as Day (D) 0.

One week later, at D 10, tail vein blood was assayed for glycemia in each individual animal using a glucometer (Glucotrend test, Roche, Mannheim, Germany). Animals showing a value below 260 mg/dl were excluded from the study. Glycemia was checked again at D 40, at the end of the experiment.

Treatment (vehicle and IL-6) was performed from D 11 to D 40.

Planning of Experiments

Body weight and survival rate were recorded every day.

Tail flick and EMG testings were performed once a week as following timing:

D-7: baseline (tail flick, locomotor activity and EMG)
D 0: induction of diabetes by STZ injection
D 10: measure of glycemia
D 11: onset of the treatment (IL-6)
D 24: tail flick test
D 25: locomotor activity in OF (open field)
D 26: EMG testing
D 38: tail flick test
D 39: locomotor activity in OF D 40: control of glycemia, EMG testing, removal of sciatic nerve Sensitivity Test: Tail Flick The tail of the rat was placed under a shutter-controlled lamp as a heat source (Bioseb, Paris, France). The latency before the rat flicked its tail from the heat was recorded. A sensory alteration increases the latency of flick. Two trials were performed and the mean value was calculated and retained as characteristic value.

Locomotor Activity in Open Field

The animal was placed in a Plexiglas (80×80×40 cm) open field (OF). The floor was divided into 16 equal squares. For each animal, the spontaneous locomotor activity and the number of rearings were recorded during a 10 min period.

Electromyography

Electrophysiological recordings were performed using a Neuromatic 2000M electromyograph (EMG) (Dantec, Les Ulis, France). Rats were anaesthetized by intraperitoneal injection of 60 mg/kg ketamine chlorhydrate (Imalgene 500®, Rhone Mérieux, Lyon, France). The normal body temperature was maintained at 30° C. with a heating lamp and controlled by a contact thermometer (Quick, Bioblock Scientific, Illkirch, France) placed on the tail surface.

Compound muscle action potential (CMAP) was recorded in the gastrocnemius muscle after stimulation of the sciatic nerve. A reference electrode and an active needle were placed in the hindpaw. A ground needle was inserted on the lower back of the rat. Sciatic nerve was stimulated with a single 0.2 ms pulse at a supramaximal intensity. The velocity of the motor wave was recorded and expressed in ms.

Sensitive nerve conduction velocity (SNCV) was also recorded. The tail skin electrodes were placed as follows: a reference needle inserted at the base of the tail and an anode needle placed 30 mm away from the reference needle towards the extremity of the tail. A ground needle electrode was inserted between the anode and reference needles. The caudal nerve was stimulated with a series of 20 pulses (for 0.2 ms) at an intensity of 12.8 mA. The velocity was expressed in m/s.

Morphometric Analysis

Morphometric analysis was performed at the end of the study (D 40). The animals were anesthetized by IP injection of 100 mg/kg Imalgène 500®. A 5 mm-segment of sciatic nerve was excised for histology. The tissue was fixed overnight with 4% glutaraldehyde (Sigma, L'Isle d'Abeau-Chesnes, France) solution in phosphate buffer solution (pH=7.4) and maintained in 30% sucrose at +4° C. until use. The nerve sample was fixed in 2% osmium tetroxide (Sigma, L'Isle d'Abeau-Chesnes, France) solution in phosphate buffer solution for 2 h., dehydrated in serial alcohol solution, and embedded in Epon. Embedded tissues were then placed at +70° C. during 3 days of polymerization. Transverse sections of 1.5 μm were cut with a microtome, stained with a 1% toluidine blue solution (Sigma, L'Isle d'Abeau-Chesnes, France) for 2 min, dehydrated and mounted in Eukitt. Twenty sections per sample were examined using an optical microscope (Nikon, Tokyo, Japan) and 6 randomly selected slices were analyzed using a semi-automated digital image analysis software (Biocom, France). Two randomly selected fields per slice were studied. The following parameters were calculated: (a) fiber diameter, (b) axon diameter, (c) myelin thickness.

For counting the total number of fibers per nerve section, 3 randomized slices per sample were selected and 2 fields per slice were analyzed.

Data Analysis

Global analysis of the data was performed using one factor or repeated measure analysis of variance (ANOVA) and one way ANOVA. Dunnett's test was used when anova test indicated a significant difference. No post-hoc analyses were performed. The level of significance was set at $p<0.05$. Results are expressed as mean±standard error of the mean (s.e.m.).

Results

Study A

Animal Weight

Figure 11:
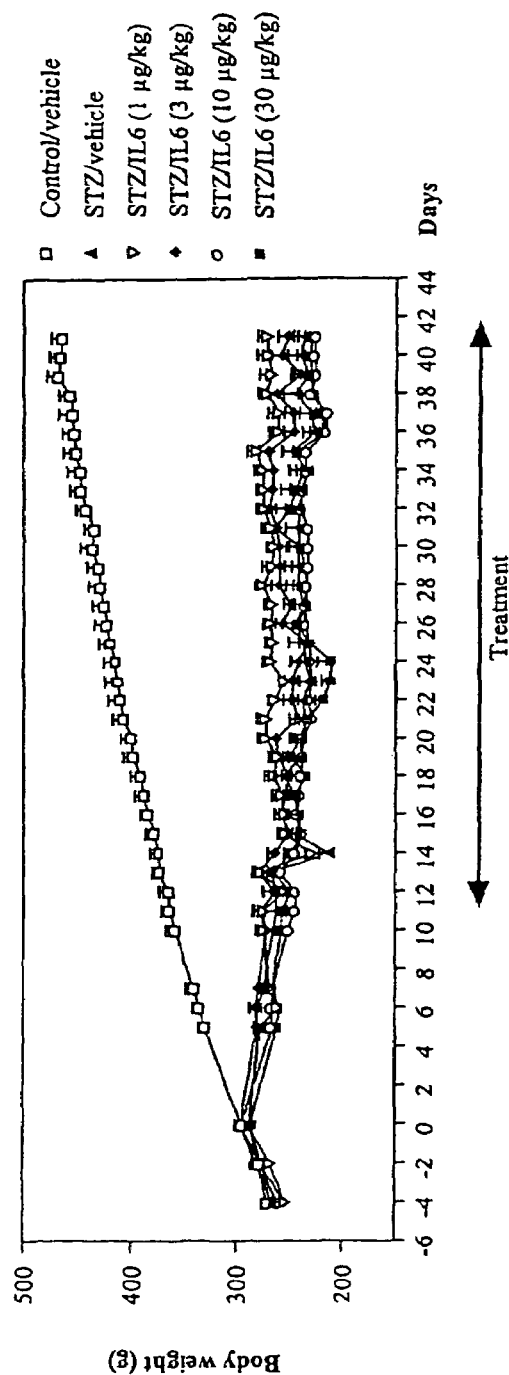
FIG. 11 shows the development of body weight in experimental animals of group A of animals receiving subcutaneous administration.

As illustrated in FIG. 11, a significant intergroup difference in body weight evolution was noted in this study $[f (5, 185)=9.20$ and $p<0.001$; repeated measure anova]. from d 5 to d 40, the STZ-intoxicated/IL-6-treated animals displayed a significant decrease in body weight ($p<0.05$; one way ANOVA and $p<0.05$ control versus (vs) STZ; control vs STZ+il-6; dunnett's test).

Diabetic animals treated with il-6 at a dose of 10 μg/kg displayed a body weight significantly higher than that of other doses of il-6 $[f (4, 148)=2.93$ and $p<0.001$; repeated measures ANOVA].

Glycemia

Figure 12:
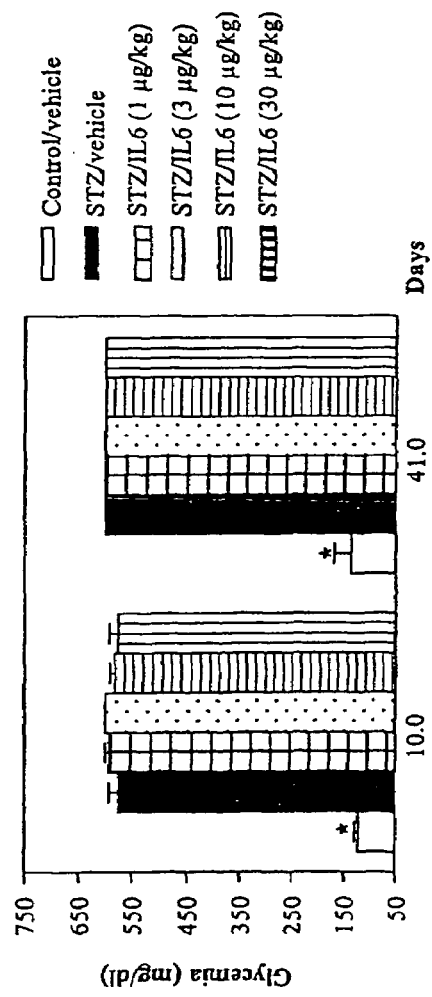
FIG. 12 shows the extent of glycemia after day 10 and day 41 of diabetes induction in experimental animals of group A of animals receiving subcutaneous administration.

FIG. 12 shows that at d 10 control animals presented a glycemia value equal at 120 mg/dl. On the other hand, STZ-intoxicated rats displayed a plasma glucose concentration higher than 260 mg/dl and were considered as diabetic.

It was noted that STZ-intoxicated rats were still diabetic at d 41 (the rat no 2 of the stz/IL-6 (10 μg/kg) group has been eliminated of the study because of his glycemia below 260 mg/dl).

Sensitivity Test: Tail Flick

Figure 13:
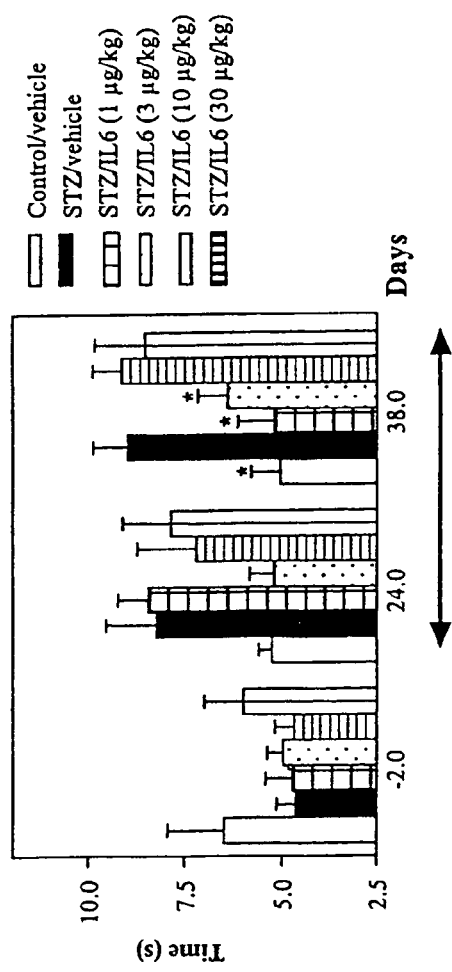
FIG. 13 shows the time to flick their tail placed on a heat source in seconds by experimental animals of group A of animals receiving subcutaneous administration.

There was no significant intergroup difference in the evolution of tail-flick test performances $[F (5, 10)=1.81$ and $p=0.072$; repeated measure ANOVA] (FIG. 13). Nevertheless, the latency before the rats flicked their tail from the heat was increased in diabetic non treated and treated with IL-6 at higher doses animals. In the D 38, the reaction time was not increased in the animals treated with IL-6 at doses of 1 and 3 μg/kg. Indeed, no significant difference between these groups was found ($p>0.05$; Dunnett's test).

Locomotor Activity in OF

Figure 14:
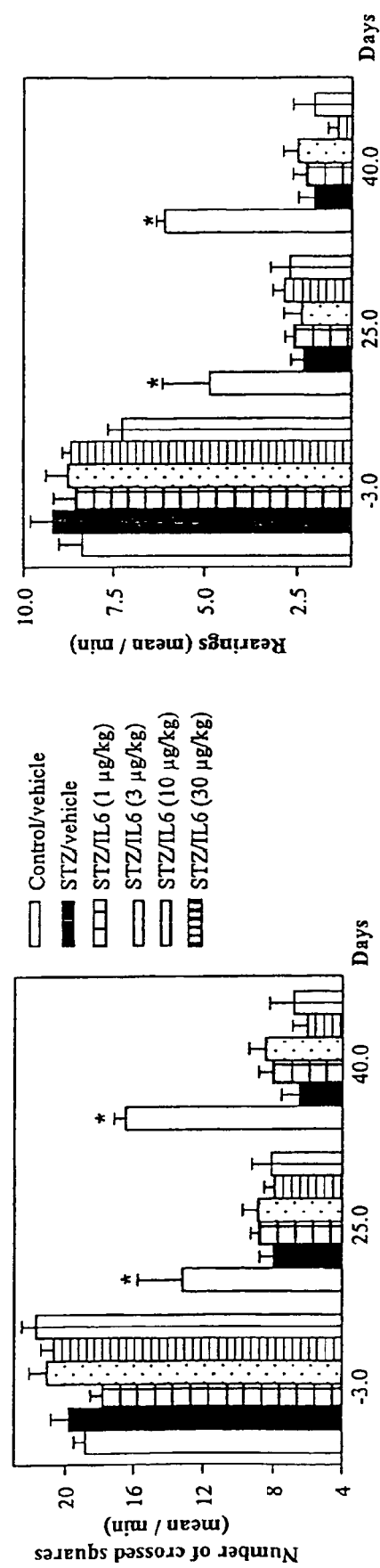
FIG. 14 shows the number of crossed squares (A) and rearings (B) in experimental animals of group A of animals receiving subcutaneous administration.

As shown in FIGS. 14A and 14B, there was a significant difference between the groups in the number of crossed squares and rearings throughout the study [respectively, $F (5, 10)=5.99$ with $p<0.001$ and $F (5, 10)=4.22$ with $p<0.001$; repeated measures ANOVA]. On day 25 and 40, diabetic, treated or not, displayed a lower locomotor activity which was characterized by a significant decrease of numbers of crossed squares and rearings (control vs STZ/vehicle and control vs STZ/IL-6 $p<0.01$; Dunnett's test).

It could be noted that the animals treated with the doses of 1 and 3 μg/kg presented a higher locomotor activity than the STZ/vehicle rats.

Electrophysiological Measurements

Latency of the Compound Muscle Action Potential

Figure 15:
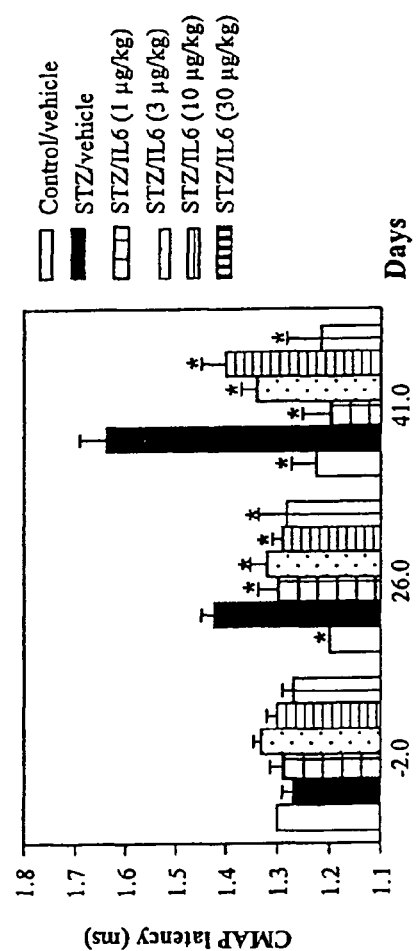
FIG. 15 shows the compound muscle action potential (CMAP) expressed in latency per second in experimental animals of group A of animals receiving subcutaneous administration.

There was a significant difference between the groups in the latency of the CMAP throughout the study $[F (5, 10)=5.71$ and $p<0.001$; repeated measures ANOVA]. The latency was significantly increased in diabetic untreated rats (on days 26 and 41 $p<0.01$; one way ANOVA). Moreover, this increase was less important in each IL-6-treated groups (FIG. 15).

On days 26 and 41, each STZ/IL-6-treated groups displayed a CMAP latency significantly shorter than the CMAP latency of the STZ/vehicle group ($p=0.05$, Dunnett's test).

Sensory Nerve Conduction Velocity

Figure 16:
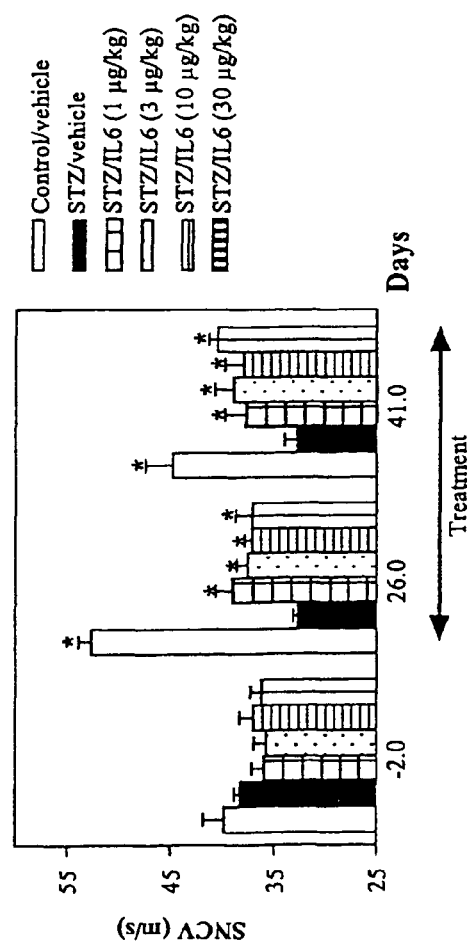
FIG. 16 shows the sensory nerve conduction velocity (SNVC) in m/sec experimental animals of group A of animals receiving subcutaneous administration.

A significant difference was noted between the groups in the SNCV throughout the study $[F (5,10)=3.78$ and $p<0.001$;

repeated measures ANOVA] (FIG. 16). Diabetic rats displayed a significant decrease of the SNCV (on days 26 and 41: p<0.01; one way ANOVA) in contrast with the control/vehicle group.

On days 26 and 41, all the IL-6 treated animals displayed a significant difference with the STZ/vehicle group (p<0.05; Dunnett's test). Moreover, on day 41 no significant difference was observed between the control/vehicle group and the 3 and 30 µg/kg IL-6-treated groups (respectively, p=0.054 and p=0.184; Dunnett's test), whereas a significant difference was seen between all the other groups.

Morphometric Analysis

Fiber Diameter

Figure 17:
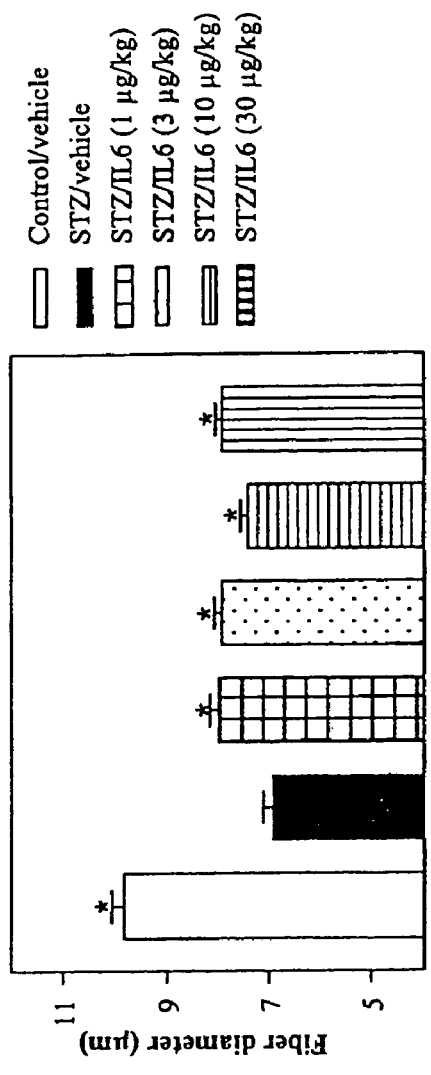
FIG. 17 shows the fiber diameter in micrometers in experimental animals of group A of animals receiving subcutaneous administration.

As shown in FIG. 17, a significant intergroup difference was seen in fiber diameter (p<0.001; one way ANOVA). A decrease of fiber diameter was observed in diabetic rats in comparison with control/vehicle group (p<0.001; Dunnett's test). Moreover, IL-6 treatment, for all tested doses significantly prevents from this diameter decrease (STZ/vehicle vs STZ/IL-6 treated: p<0.05; Dunnett's test).

Axon Diameter

Figure 18:
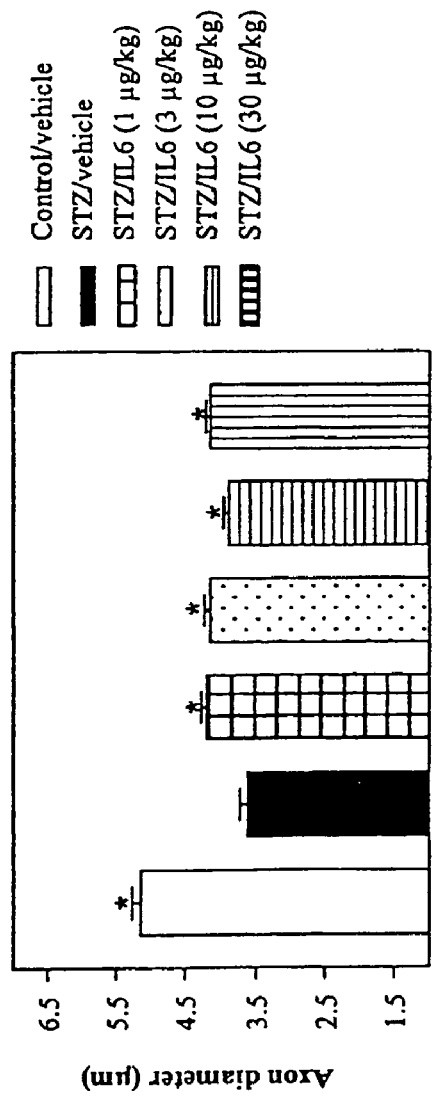
FIG. 18 shows the axon diameter in micrometers in experimental animals of group A of animals receiving subcutaneous administration.

There was a significant difference between groups in axon diameter (p<0.001; one way ANOVA) (FIG. 18). STZ/vehicle group displayed a significant decrease of axon diameter (control/vehicle vs STZ/vehicle: p<0.001; Dunnett's test). Animals treated with IL-6 at all tested doses presented an axon diameter significantly higher than diabetic non treated rats (p<0.05; Dunnett's test).

Myelin Thickness

Figure 19:
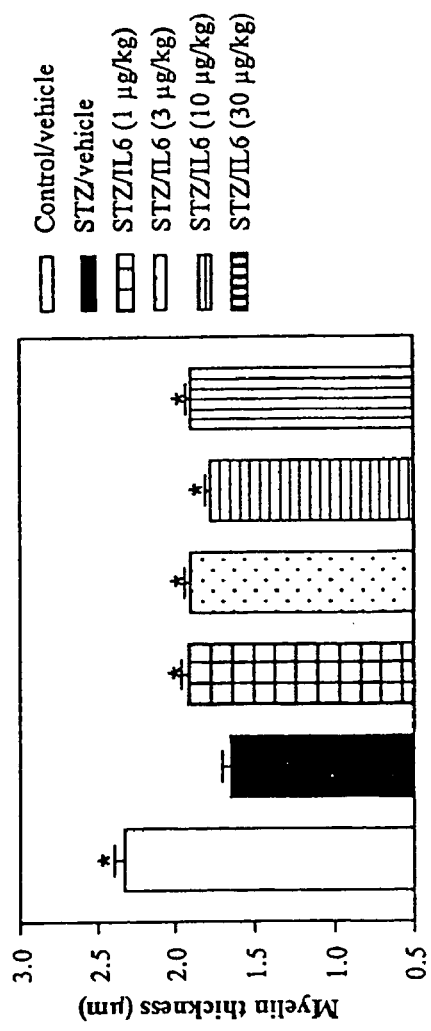
FIG. 19 shows the myelin thickness in micrometers in experimental animals of group A of animals receiving subcutaneous administration.

A significant intergroup difference was found in myelin thickness (p<0.001; one way ANOVA) (FIG. 19). A significant decrease of myelin thickness was observed in diabetic rats in comparison with control/vehicle animals (p<0.001; Dunnett's test). Moreover, this decrease was significantly less important in IL-6-treated groups (p<0.05; Dunnett's test).

Percentage of Degenerate Fibers

Figure 20:
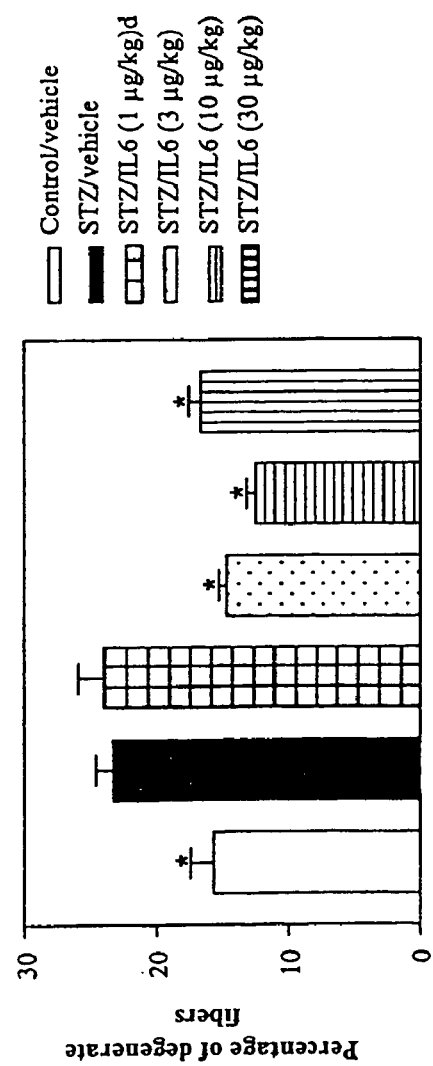
FIG. 20 shows the percentage of degenerate fibers in experimental animals of group A of animals receiving subcutaneous administration.
Figure 21:
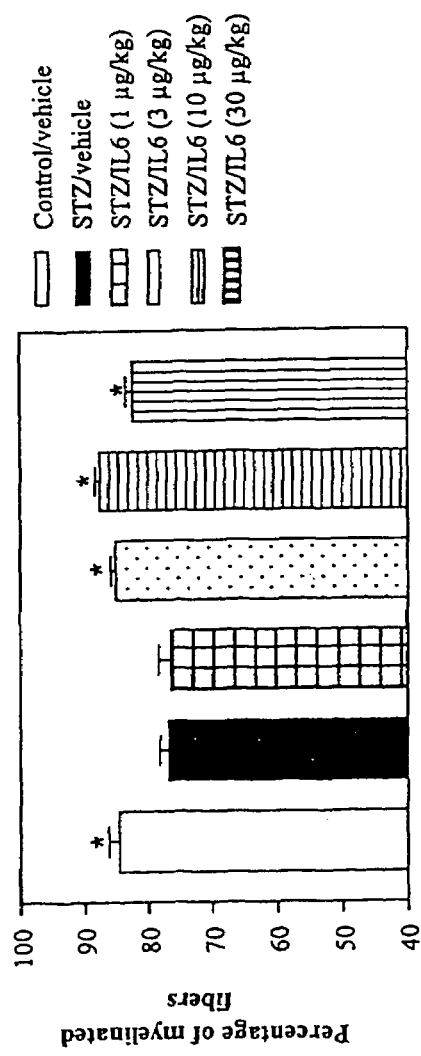
FIG. 21 shows the percentage of myelinated fibers in experimental animals of group A of animals receiving subcutaneous administration.

As shown in FIGS. 20 and 21, diabetic and no-treated rats dispalyed a significant decrease of myelinated fibers (p<0.001; one way ANOVA). Treatment with IL-6 at doses of 3, 10 and 30 µg/kg every day, decreased significantly the percentage of degenerate fibers in comparison with STZ/vehicle group (p<0.001; Dunnett's test).

Study B

Animal Weight

Figure 22:
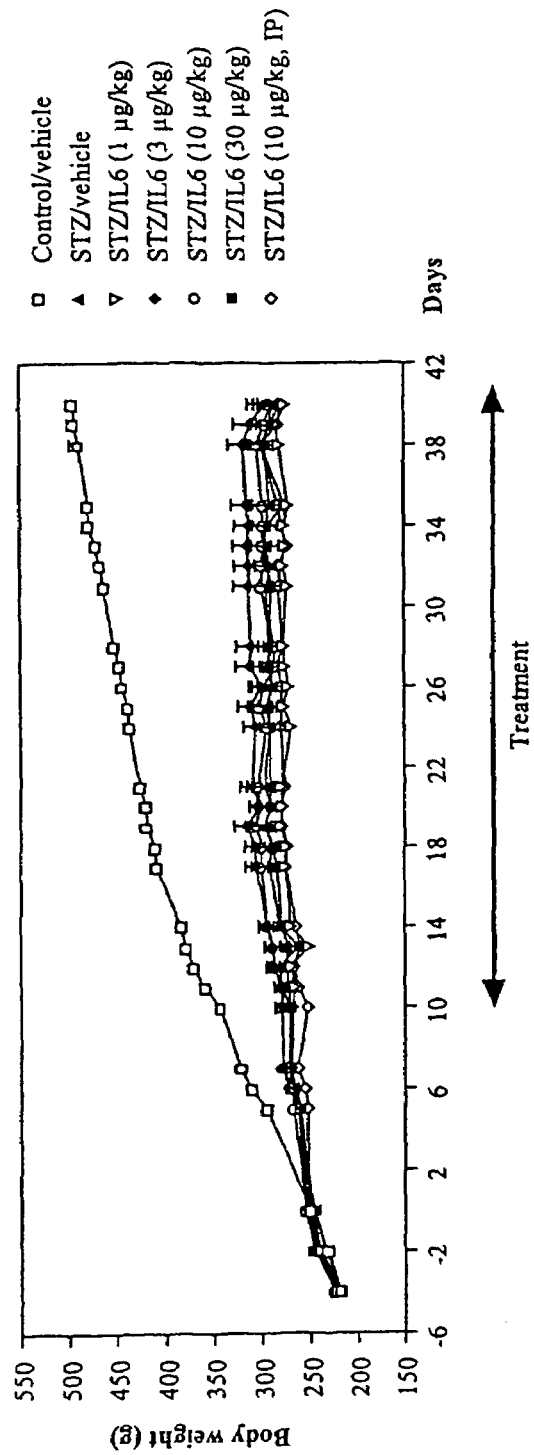
FIG. 22 shows the development of body weight in experimental animals of group B of animals receiving subcutaneous administration.

There was a significant intergroup difference in body weight evolution [F (6, 168)=9.24 and p<0.001; repeated measures ANOVA] (FIG. 22). From D 5 to D 40, the STZ-intoxicated animals displayed a significant decrease in body weight (p<0.05; one way ANOVA and p<0.001 control/vehicle vs STZ; control/vehicle vs STZ-IL-6-treated groups; Dunnett's test).

No significant difference was found between the STZ/IL-6-treated groups in the body weight from D 5 to D 40 [F (5, 125)=1.08 and p=0.26; repeated measures ANOVA].

Glycemia

Figure 23:
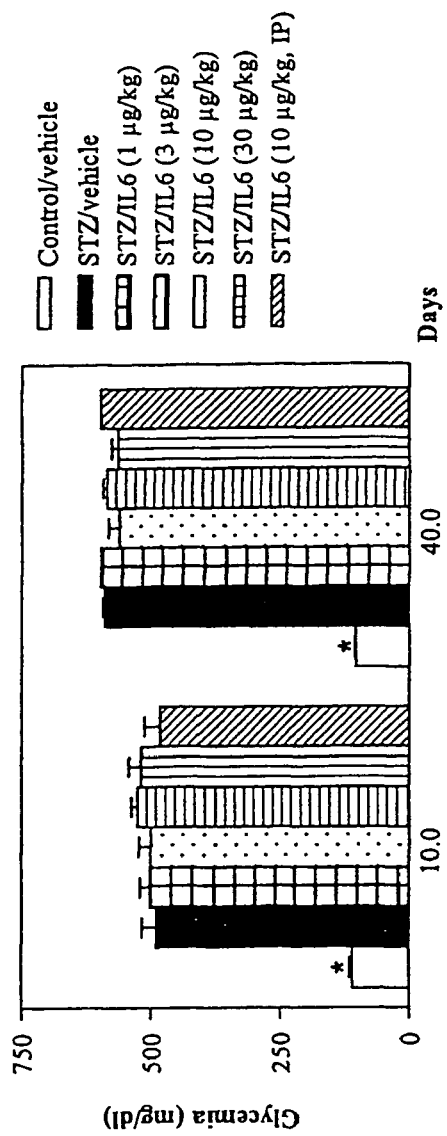
FIG. 23 shows the extent of glycemia after day 10 and day 40 of diabetes induction in experimental animals of group B of animals receiving subcutaneous administration.

As illustrated in FIG. 23, at D 10 STZ-intoxicated rats displayed a plasma glucose concentration higher than 260 mg/dl whereas control animals presented a glycemia value around 100 mg/dl.

Moreover, at D 40 STZ-intoxicated rats were still diabetic, indeed their glycemia was higher than 500 mg/dl.

Sensitivity Test: Tail Flick

Figure 24:
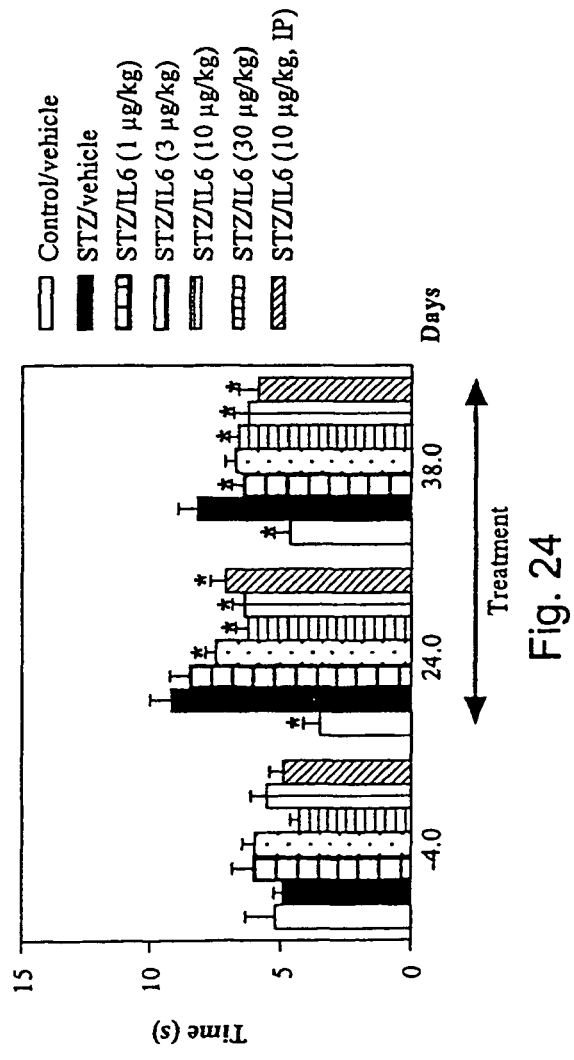
FIG. 24 shows the time to flick their tail placed on a heat source in seconds by experimental animals of group B of animals receiving subcutaneous administration.

There was a significant intergroup difference in the evolution of tail flick test performances [F (6, 12)=2.13 and p=0.02; repeated measures ANOVA] (FIG. 24). At days 24 and 38, diabetic and non-treated rats displayed a significant increased reaction time in comparison with the control/vehicle and STZ/IL-6-treated groups (p<0.05; Dunnett's test).

Moreover, the reaction time was less increased in the animals treated with IL-6 at doses of 10 and 30 µg/kg.

Locomotor Activity in OF

Figure 25:
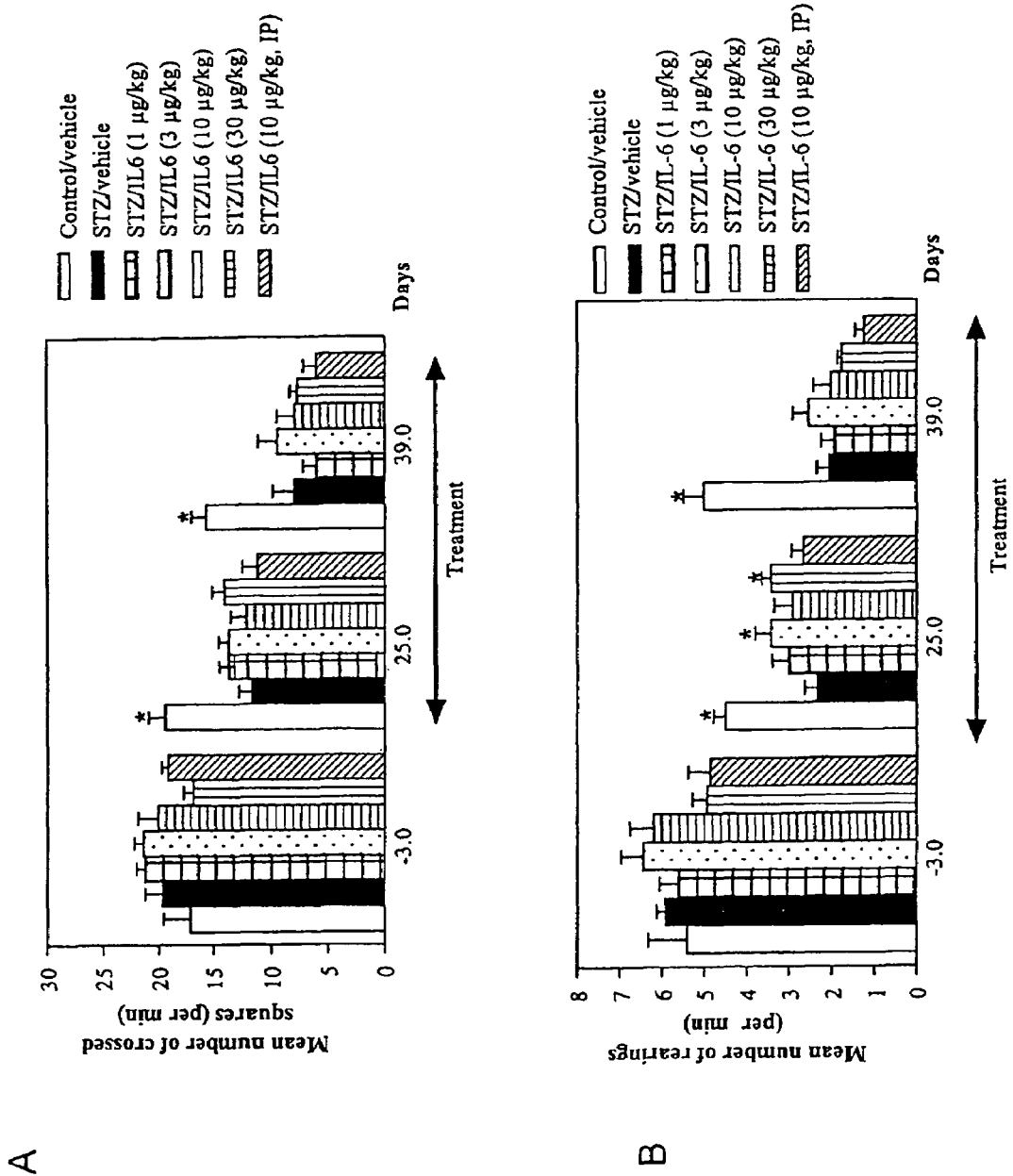
FIG. 25 shows the number of crossed squares (A) and rearings (B) in experimental animals of group B of animals receiving subcutaneous administration.

As shown in FIGS. 25A and 25B, there was a significant difference between the groups in the number of crossed squares and rearings throughout the study. On day 25 and 40, diabetic, treated or not, displayed a lower locomotor activity which was characterized by a significant decrease of numbers of crossed squares and rearings (control vs STZ/vehicle and control vs STZ/IL-6 p<0.01; Dunnett's test).

Electrophysiological Measurements

Latency of the Compound Muscle Action Potential

Figure 26:
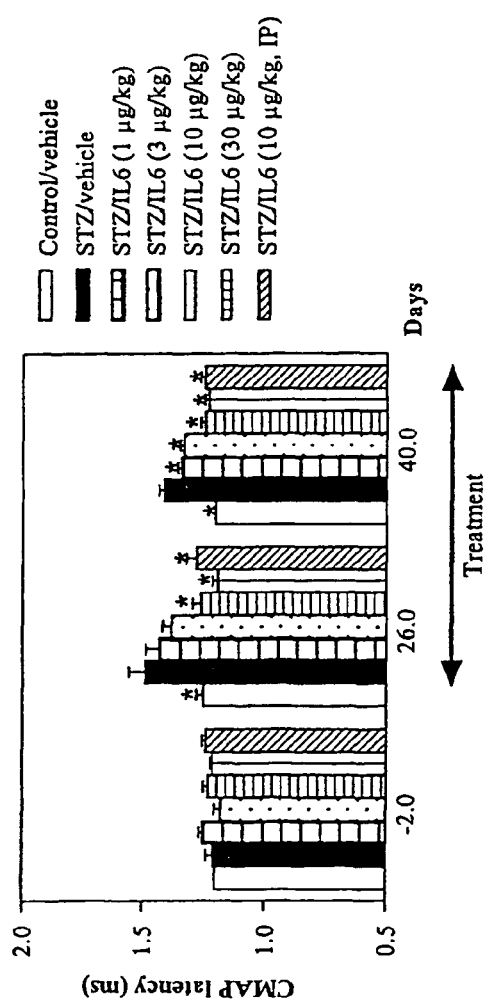
FIG. 26 shows the compound muscle action potential (CMAP) expressed in latency per second in experimental animals of group B of animals receiving subcutaneous administration.

As shown in FIG. 26, there was a significant difference between the groups in the latency of the CMAP throughout the study [F (6, 12)=3.97 and p<0.001; repeated measures ANOVA]. On D 26 and D 40, a significant increase of the latency was observed in the diabetic non-treated rats and the animals treated with IL-6 at low dose (p<0.001; one way ANOVA). Moreover, no significant difference was found between the control/vehicle and STZ/IL-6 treated (10 and 30 µg/kg) groups (p>0.05; one way ANOVA).

Sensory Nerve Conduction Velocity

Figure 27:
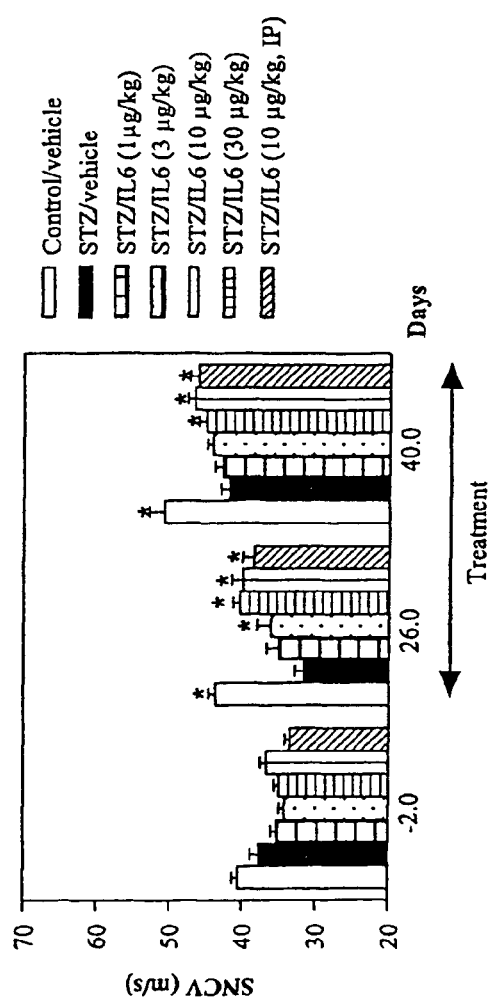
FIG. 27 shows the sensory nerve conduction velocity (SNVC) in m/sec experimental animals of group B of animals receiving subcutaneous administration.

There was a significant difference between the groups in the SNCV measure throughout the study [F (6, 12)=3.38 and p<0.001; repeated measures ANOVA] (FIG. 27) Since D 26, diabetic and treated or not rats displayed a decrease of the SNCV (D 26: p<0.001 and D 40 p<0.001; one way ANOVA).

On D 26, the control/vehicle and STZ/IL-6 treated animals displayed a SNCV significantly higher than that of STZ/vehicle rats (p<0.05; Dunnett's test).

On D 40, The rats treated with IL-6 at higher doses presented a value of SNCV more important than that of STZ/vehicle group.

Morphometric Analysis

Fiber Diameter

Figure 28:
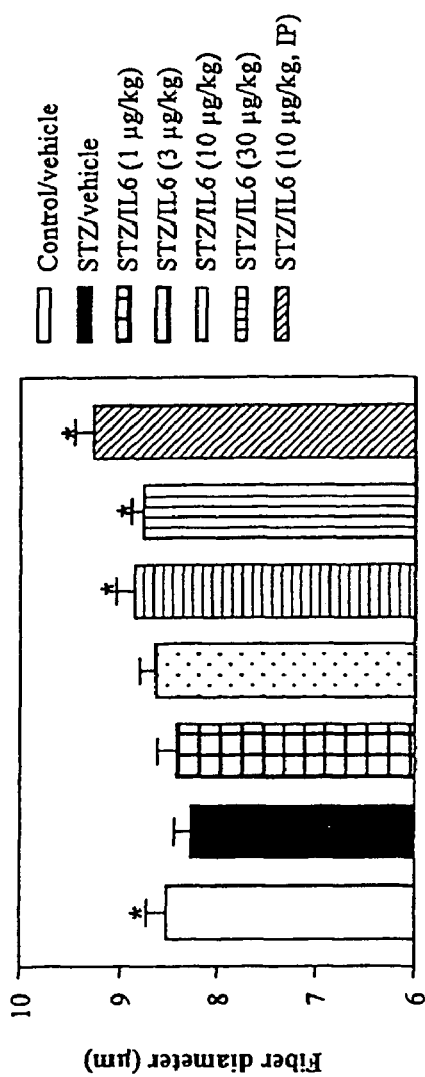
FIG. 28 shows the fiber diameter in micrometer in experimental animals of group B of animals receiving subcutaneous administration.

As shown in FIG. 28, a significant intergroup difference was noted in fiber diameter (p=0.045; one way ANOVA). STZ-intoxicated animals displayed a significant decrease of fiber diameter in comparison with control/vehicle rats (p<0.05; Dunnett's test). Daily IP treatment with IL-6 prevented from this fiber diameter decrease (STZ/vehicle vs STZ/IL-6 IP: p=0.026; Dunnett's test).

Axon Diameter

Figure 29:
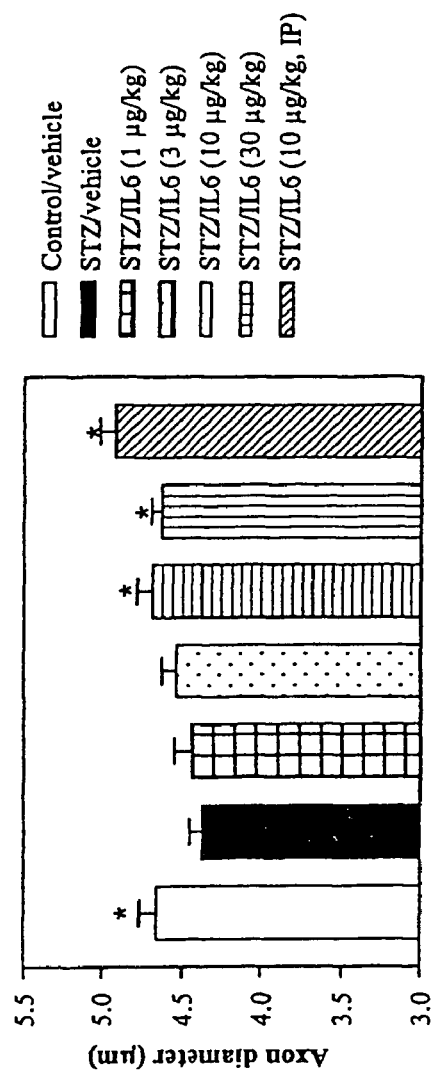
FIG. 29 shows the axon diameter in micrometer in experimental animals of group B of animals receiving subcutaneous administration.

There was a significant difference between groups in axon diameter (p=0.034; one way ANOVA) (FIG. 29). A significant decrease of axon diameter was observed in STZ-intoxicated animals (p<0.05; Dunnett's test). Rats treated with IL-6 at 10 µg/kg by IP route displayed a significant difference with STZ/vehicle animals (p=0.045; Dunnett's test).

Myelin Thickness

Figure 30:
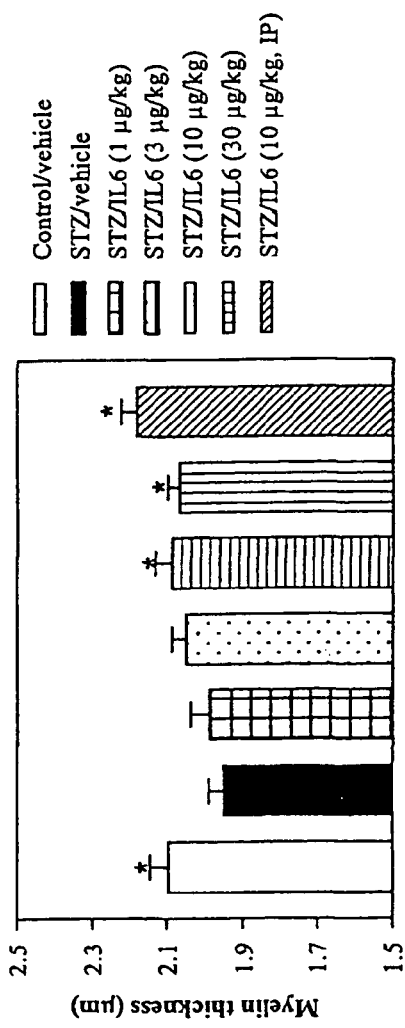
FIG. 30 shows the myelin thickness in micrometers in experimental animals of group B of animals receiving subcutaneous administration.

A significant intergroup was found in myelin thickness (p=0.05; one way ANOVA) (FIG. 30). STZ-intoxicated animals displayed a significant decrease of myelin thickness (p<0.05; Dunnett's test). A daily IP treatment with IL-6 prevented from this decrease of myelin thickness (STZ/vehicle vs STZ/IL-6 IP: p<0.005; Dunnett's test).

Percentage of Degenerate Fibers

Figure 31:
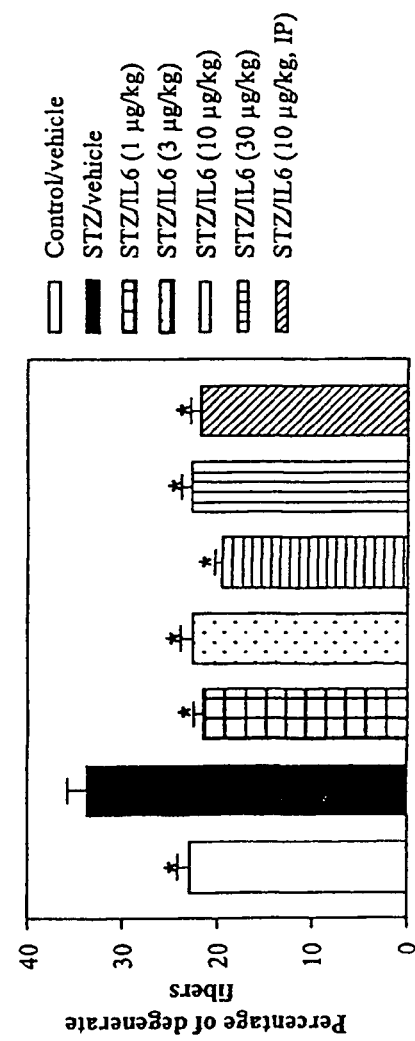
FIG. 31 shows the percentage of degenerate fibers in experimental animals of group B of animals receiving subcutaneous administration.
Figure 32:
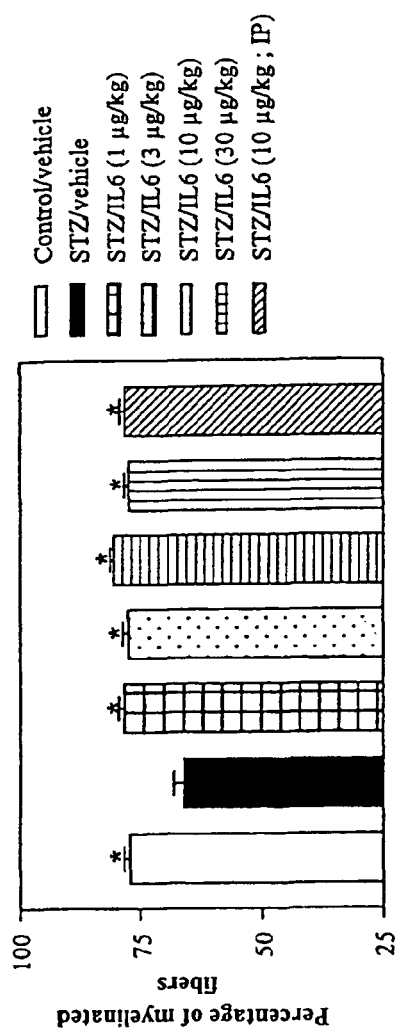
FIG. 32 shows the percentage of myelinated fibers in experimental animals of group B of animals receiving subcutaneous administration.

As illustrated in FIGS. 31 and 32, a significant intergroup difference in percentage of degenerate fibers was found (p<0.001; one way ANOVA). This percentage was significantly higher in STZ/vehicle group than control/vehicle one (p<0.001; Dunnett's test). Percentage was significantly decreased in IL-6-treated animals (STZ/vehicle vs STZ/IL-6: p<0.001; Dunnett's test).

Study C

Animal Weight

Figure 33:
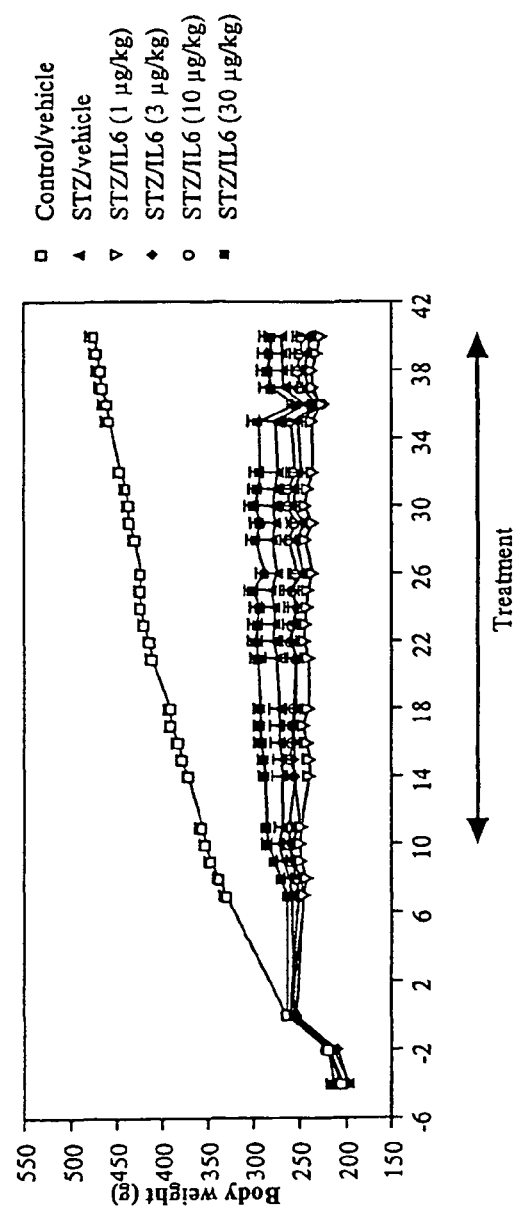
FIG. 33 shows the development of body weight in experimental animals of group C of animals receiving subcutaneous administration.

As illustrated in FIG. 33, a significant intergroup difference in body weight evolution was observed throughout the study [$F (5, 145)=15.46$ and $p<0.001$; repeated measures ANOVA]. From D 5 to D 40, the STZ-intoxicated animals displayed a significant decrease in body weight ($p<0.001$; one way ANOVA and $p<0.001$ control/vehicle vs STZ; control/vehicle vs STZ-IL-6-treated groups; Dunnett's test).

Moreover, the animals treated with IL-6 at 30 µg/kg displayed a decrease of body weight significantly less important than the others IL-6 treated groups [$F (4, 104)=2.17$ and $p<0.001$; repeated measures ANOVA].

Glycemia

Figure 34:
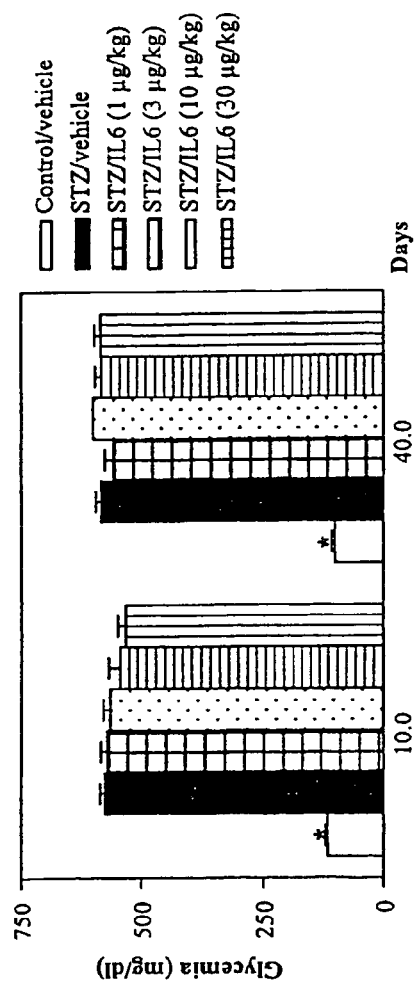
FIG. 34 shows the extent of glycemia after day 10 and day 40 of diabetes induction in experimental animals of group C of animals receiving subcutaneous administration.

FIG. 34 shows that control/vehicle group presented a glycemia value inferior at 120 mg/dl on D 10 and D 40. On the other hand, STZ-intoxicated rats displayed a plasma glucose concentration higher than 260 mg/dl, so they were considered as diabetic on D 10 and D 40.

Sensitivity Test: Tail Flick

Figure 35:
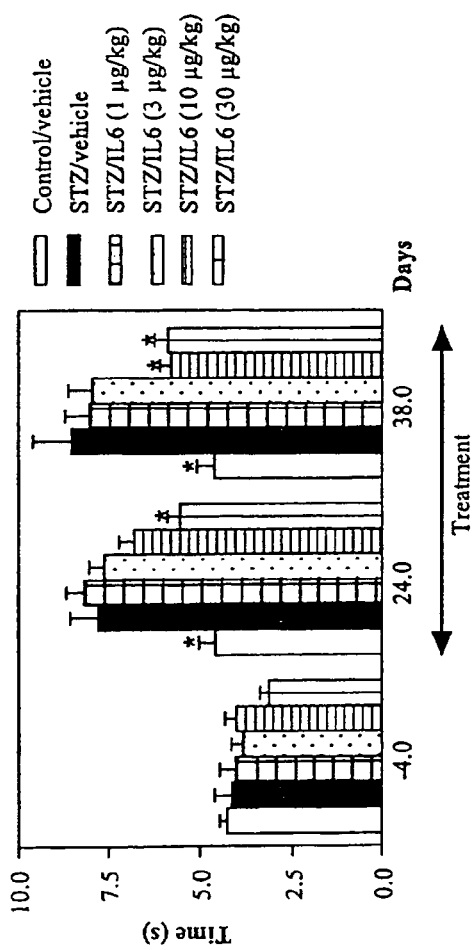
FIG. 35 shows the time to flick their tail placed on a heat source in seconds by experimental animals of group C of animals receiving subcutaneous administration.

There was a significant intergroup difference in the reaction time throughout the study [$F (5, 10)=2.30$ and $p=0.02$; repeated measures ANOVA] (FIG. 35). The latency before the rats flicked their tail from the heat was significantly increased in STZ/vehicle animals (on D 24 and D 38: $p<0.005$; one way ANOVA). On D 24, there was no significant difference in the latency of reaction between the control/vehicle and STZ/IL-6 (30 µg/kg) groups ($p=0.31$; Dunnett's test). On D 38, the rats treated with IL-6 at 10 and 30 µg/kg displayed a reaction time similar to control one ($p=0.3$; Dunnett's test).

Locomotor Activity in OF

Figure 36:
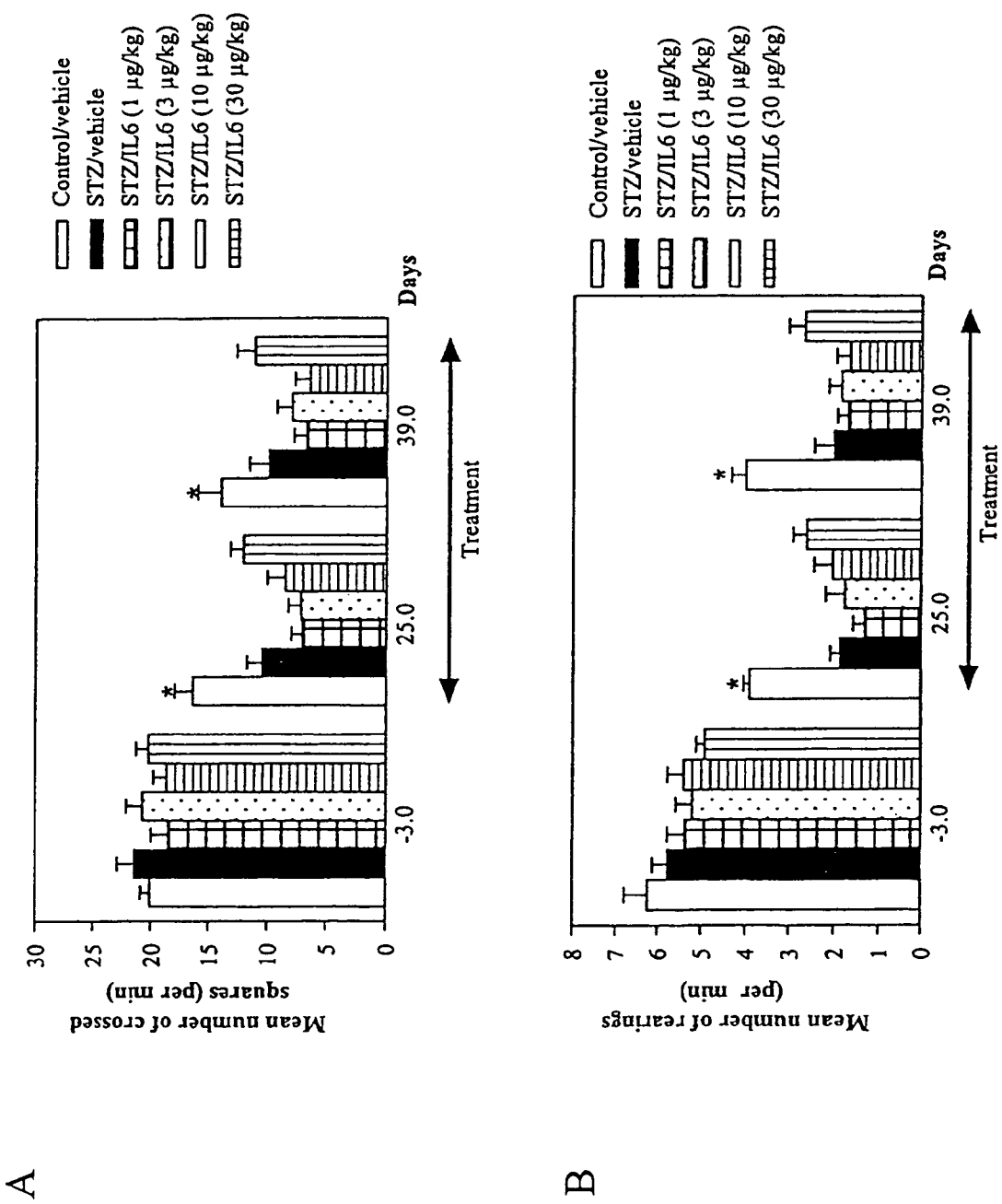
FIG. 36 shows the number of crossed squares (A) and rearings (B) in experimental animals of group C of animals receiving subcutaneous administration.

On D 25 and D 39 (FIGS. 36A and 36B), STZ-intoxicated, treated or not, animals displayed a significant lower locomotor activity than the control rats one ($p<0.05$; Dunnett's test). This difference was noted in the mean number of crossed squares and the number of rearings throughout the recorded period. Nevertheless, the group of animals treated with IL-6 at the dose of 30 µg/kg presented a larger locomotor activity than STZ/vehicle group.

Electrophysiological Measurements

Latency of the Compound Muscle Action Potential

Figure 37:
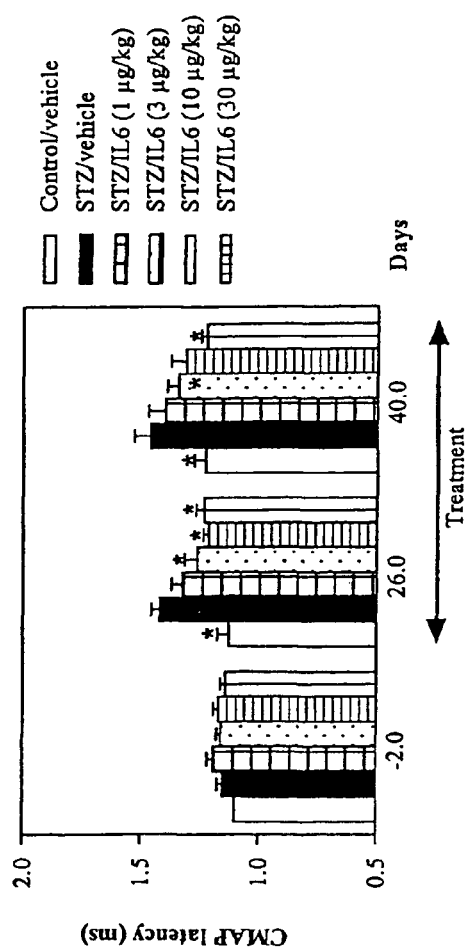
FIG. 37 shows the compound muscle action potential (CMAP) expressed in latency per second in experimental animals of group C of animals receiving subcutaneous administration.

No significant inter group difference was noted in the latency of the OMAP throughout the study [$F (5, 10)=1.33$ and $p=0.23$; repeated measures ANOVA] (FIG. 37). Nevertheless, a significant difference between the groups was observed on D 26 and D 40 ($p<0.05$; one way ANOVA). STZ-intoxicated rats displayed an increased latency in comparison with the control/vehicle group. Moreover, this increase was less important in groups treated with IL-6 at high doses, indeed a significant difference was noted between STZ/vehicle and STZ/IL-6 groups (on D 26: STZ/vehicle vs STZ/IL-6 at 3, 10, 30 µg/kg : $p<0.005$ and on D 40: STZ/vehicle vs STZ/TL6 at 30 µg/kg : $p<0.005$; Dunnett's test).

Sensory Nerve Conduction Velocity

Figure 38:
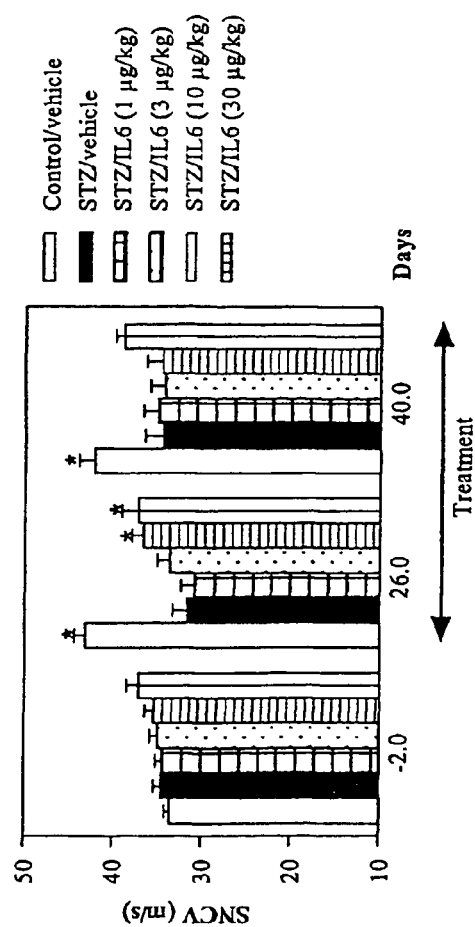
FIG. 38 shows the sensory nerve conduction velocity (SNVC) in m/sec experimental animals of group C of animals receiving subcutaneous administration.

As illustrated in FIG. 38, a significant intergroup difference was noted in the sensore nerve conduction velocity throughout the study [$F (5, 10)=2.18$ and $p=0.025$; repeated measures ANOVA]. A significant decrease of velocity was observed in STZ-intoxicated animals (control/vehicle vs STZ/vehicle and STZ/IL-6 groups: $p<0.05$; Dunnett's test). In addition, treatment with IL-6 at 10 and 30 µg/kg lead to a velocoty loss less important in diabetic animals (on D 26, STZ/IL-6 at 10 and 30 µg/kg vs STZ/vehicle: $p<0.05$; Dunnet's test).

Morphometric Analysis

Fiber Diameter

Figure 39:
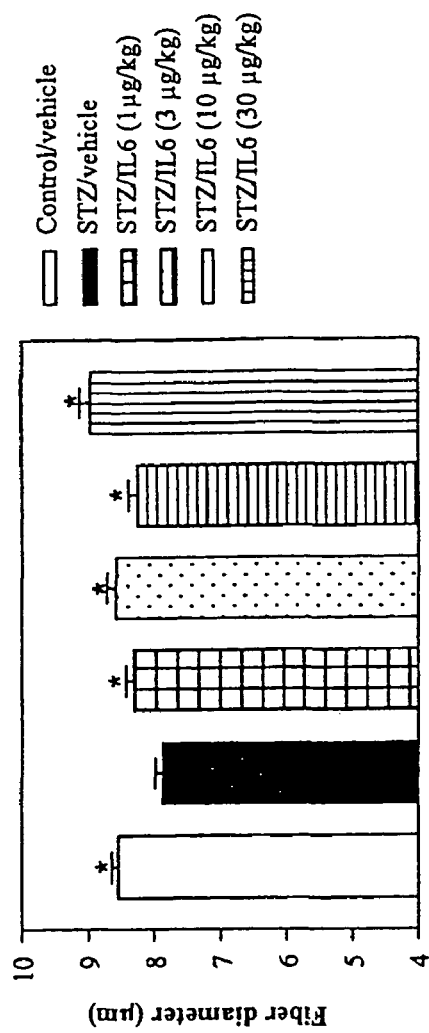
FIG. 39 shows the fiber diameter in micrometers in experimental animals of group C of animals receiving subcutaneous administration.

As shown in FIG. 39, a significant intergroup difference was noted in fiber diameter ($p<0.001$; one way ANOVA). STZ-intoxicated animals displayed a significant decrease of fiber diameter in comparison with control/vehicle rats ($p<0.005$; Dunnett's test). IL-6 treated animals (at all doses) presented a significantly higher diameter fiber than STZ/vehicle rats ($p<0.05$; Dunnett's test).

Axon Diameter

Figure 40:
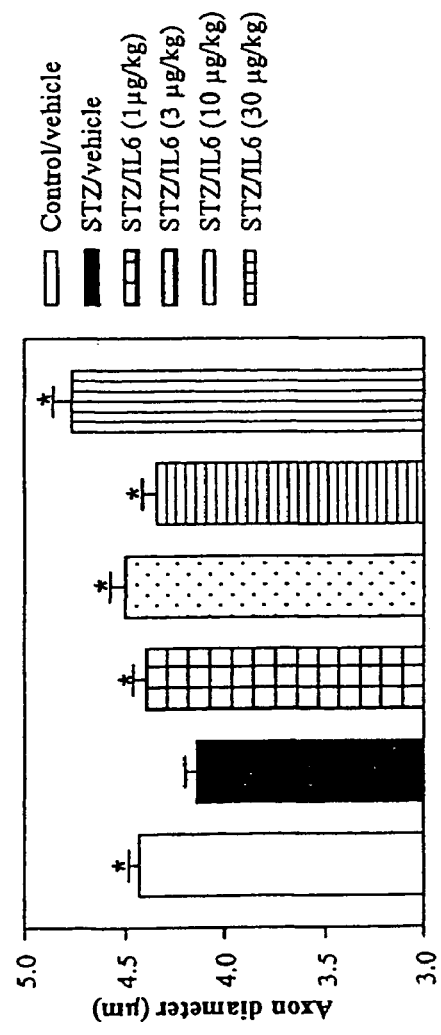
FIG. 40 shows the axon diameter in micrometers in experimental animals of group C of animals receiving subcutaneous administration.

There was a significant difference between groups in axon diameter ($p<0.001$; one way ANOVA) (FIG. 40). A significant decrease of axon diameter was observed in STZ-intoxicated animals ($p<0.01$; Dunnett's test). Rats treated with IL-6 at 1, 3, 10 and 30 µg/kg displayed a significant difference with STZ/vehicle animals ($p<0.05$; Dunnett's test).

Myelin Thickness

Figure 41:
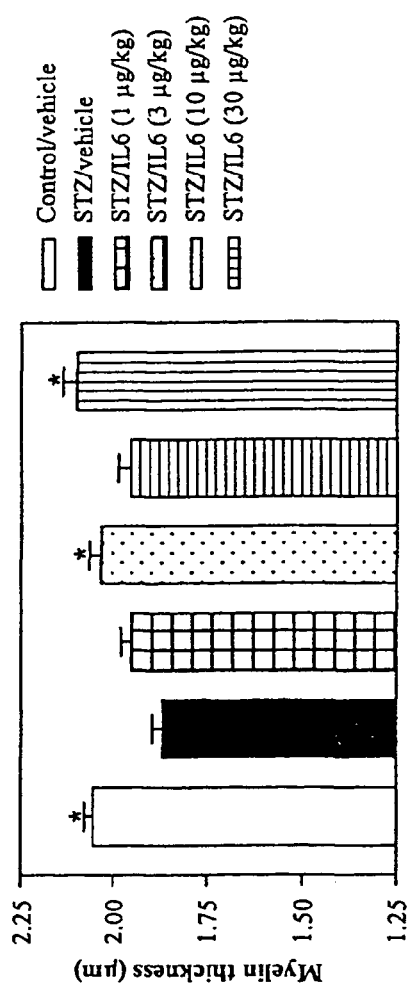
FIG. 41 shows the myelin thickness in micrometers in experimental animals of group C of animals receiving subcutaneous administration.

A significant intergroup was found in myelin thickness ($p<0.001$; one way ANOVA) (FIG. 41). STZ-intoxicated animals displayed a significant decrease of myelin thickness ($p<0.001$; Dunnett's test). A daily SC treatment with IL-6 prevented from this decrease of myelin thickness (STZ/vehicle vs STZ/IL-6 1 and 30 µg/kg: $p<0.005$; Dunnett's test).

Percentage of Degenerate Fibers

Figure 42:
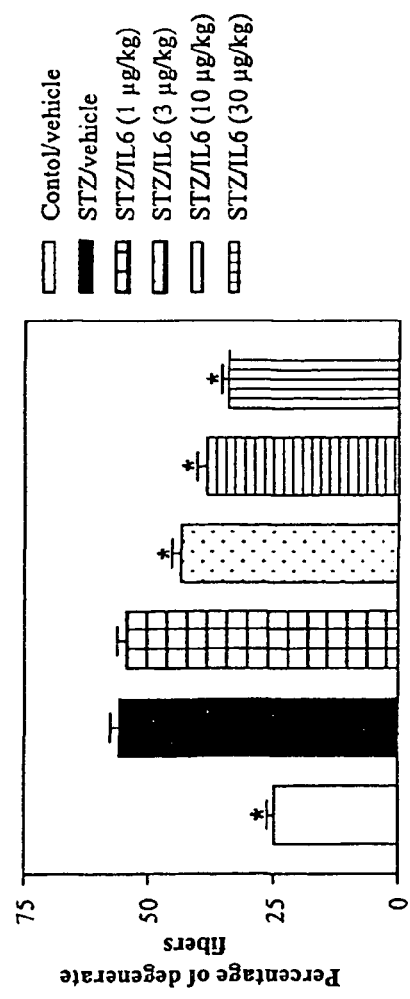
FIG. 42 shows the percentage of degenerate fibers in experimental animals of group C of animals receiving subcutaneous administration.
Figure 43:
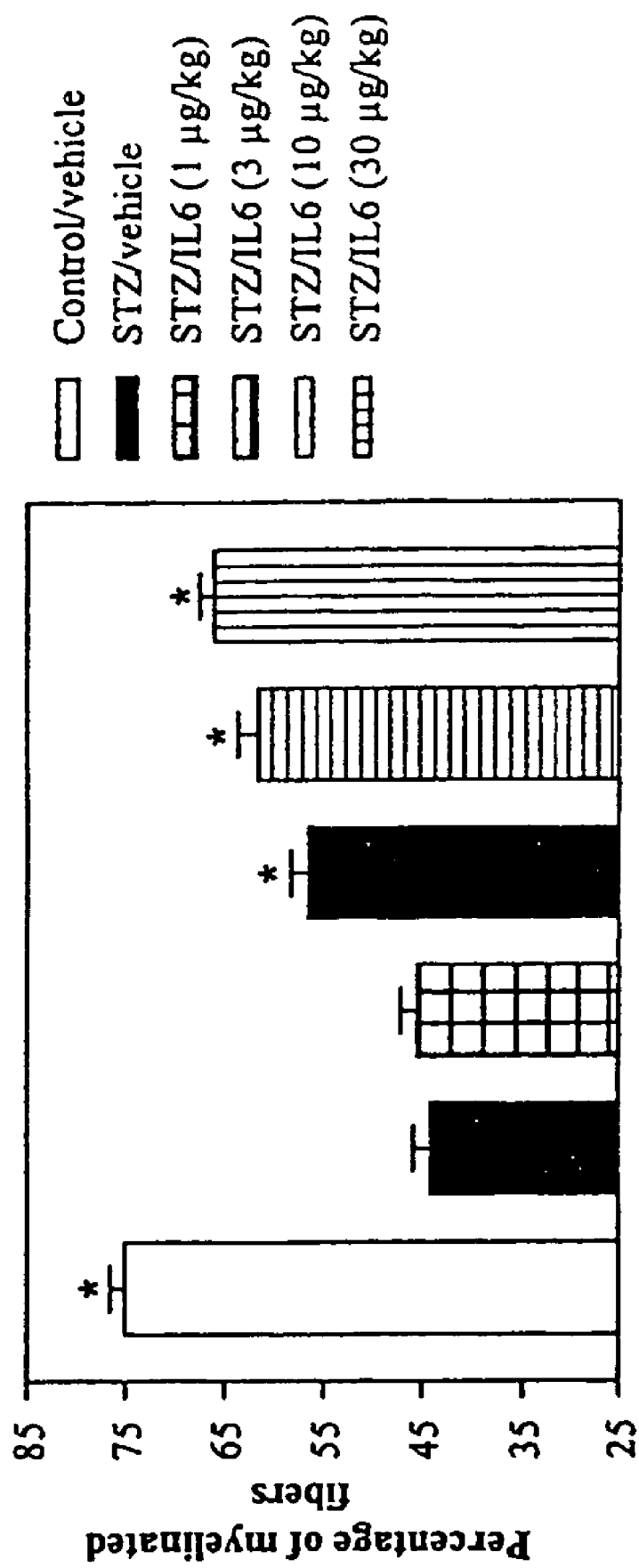
FIG. 43 shows the percentage of myelinated fibers in experimental animals of group C of animals receiving subcutaneous administration.

As illustrated in FIGS. 42 and 43, a significant intergroup difference in percentage of functional myelinated fibers was found ($p<0.001$; one way ANOVA). This percentage was significantly lower in STZ/vehicle group than control/vehicle one ($p<0.001$; Dunnett's test). Percentage was significantly increased in animals treated with IL-6 at 3, 10 and 30 µg/kg ($p<0.001$; Dunnett's test).

CONCLUSION

In this study, animals intoxicated with the streptozotocin and which develop a diabetes several days later, have been used as model of induced-neuropathy model.

The diabetic animals have been treated by different doses of IL-6 (1, 3, 10, and 30 µg/kg) on 30 days chronically. The treatment has been administrated in sub-cutaneous every day (study A), 3 times a week (study B) and once a week (study C) starting 10 days after the induction until the sacrifice of the animal 40 days after the STZ-induction. These treatments could be considered as a curative treatment, as IL-6 has been administered after the first molecular damages caused by a prolonged hyperglycemia.

The present protocol shows that a IL-6 treatment of 30 days whatever the schedule of administration, induces a neuroprotection against the diabetic neuropathy. The behavioral analyses with tail flick and the EMG testing (sensory and motor velocities) show the neuroprotective effect of IL-6 administered by subcuteanous route.

The neuroprotective effect is focused on the sensory fibers as well as motor fibers (the CMAP velocity was not altered when the animals were treated with IL-6 compound). The compound prevents fibers from loss of the myelin sheath and degeneration.

In comparison with a daily IP treatment (see previous study performed at Neurofit, August 2001), IL-6 administered daily by subcutaneous route seems to be as efficient as intraperitoneal treatment (see example 2) at all tested doses. Furthermore, a lower dosage characterized by a IL-6 administration one or three times per week, do not lead to a decrease of the neuroprotective effect of the compound. It seems that the treatment at 3 times per week displays the best neuroprotective effect (espacially at 10 and 30 µg/kg) without any side effect on the general behavioral of the STZ animals.

REFERENCES

1. Altschul S F et al, J Mol Biol, 215, 403-410, 1990
2. Altschul S F et al, Nucleic Acids Res., 25:389-3402, 1997

3. Britland S T, Young R T, Sharma A K, and Clarke B F. Diabetes, 39, 898-908. (1990)
4. Breighton, B and Hayden, M R: S Afr Med J. 1981 Feb. 21; 59(8): 250.
5. Chebath, J., Fischer, D., Kumar, A., Oh, J. W., Kollet, O., Lapidot, T., Fischer, M., Rose-John, S., Nagler, A., Slavin, S. and Revel, M. Eur. Cytokine Netw. 1997 8,359-365.
6. Devereux J et al, Nucleic Acids Res, 12, 387-395, 1984.
7. Emerich D F, Cain C K, Greco C, Saydoff J A, Hu Z Y, Liu H, Lindner M D Cell Transplant. 1997 May-June; 6(3): 249-66.
8. Emerich, D. F., Lindner, M. D., Winn, S. R., Chen, E.-Y., Frydel, B. R., and Kordower, J. H. (1996). J. Neurosci., 16, 5168-5181.
9. Emerich D F, Winn S R, Hantraye P M, Peschanski M, Chen E Y, Chu Y, McDermott P, Baetge E E, Kordower J H Nature. 1997 Mar. 27; 386(6623):395-9.
10. Emerich D F, Hammang J P, Baetge E E, Winn S R Exp Neurol. 1994 November; 130(1):141-50.
11. Fischer M, Goldschmitt J, Peschel C, Brakenhoff J P, Kallen K J, Wollmer A, Grotzinger J, Rose-John S. Nat Biotechnol. 1997 February; 15(2):142-5
12. Fisher et al., J. Neuroimmunology 119 (2001) 1-9
13. Frei et al., J. Neuroimmunol., 31:147 (1991)
14. Halimi H, Eisenstein M, Oh J, Revel M and Chebath J. Eur. Cytokine Netw. 1995, 6: 135-143,
15. Hirano et al, 1986 Nature (London) 234-73 (1986)
16. Hirano T, Matsuda T and Nakajima K: Stem cells 1994, 12:262-277.
17. Hirota H, Kiyama H, Kishimoto T. Taga T J Exp Med. 1996 Jun. 1;183(6):2627-34.
18. Ishikawa et al., 1999, Cell Mol Neurobiol. 19, 587-96
19. Lin B, Nasir J, Kalchman M A, McDonald H, Zeisler J, Goldberg Y P, Hayden M R Genomics. 1995 Feb. 10;25 (3):707-15.
20. May et al, Proc Natl Acad Sci USA 83:8957 (1986);
21. Mendel, I., Katz, A., Kozak, N., Ben-Nun, A. and Revel, M. Eur. J. Immunol. 1998 28, 1727-1737.
22. Murakami M, Hibi M, Nakagawa N, Nakagawa T, Yasukawa K, Yamanishi K, Taga T, Kishimoto T Science. 1993 Jun. 18;260(5115):1808-10.
23. Novick, D., Shulman, L. M., Chen, L. and Revel, M. Cytokine 1992 4, 6-11.
24. Novick D, Shulman L M, Chen L and Revel M. Cytokine 1992, 4: 6-11.
25. Novick D. Engelmann H. Wallach D. Leitner O. Revel M. Rubinstein M. Journal of Chromatography 1990. 510:331-7.
26. Paonessa G, Graziani R, Deserio A, Savino R, Ciapponi L, Lahmm A, Salvati A L,
27. Toniatti C and Ciliberto G. EMBO J. 1995: 14: 1942-1951.
28. Pearson W R, Methods in Enzymology, 183, 63-99, 1990
29. Pearson W R and Lipman D J, Proc Nat Acad Sci USA, 85, 2444-2448, 1988
30. Rakieten, N., Rakieten, M. L., and Nadkami, M. V., *Studies on the diabetogenic action of streptozotocin*, Cancer Chemother. Rep., 1963, 29, 91.
31. Rudas B. Streptozotocin. Azmeimittel-Forschung, 22, 830-861. (1972)
32. Smith and Waterman J Mol Biol, 147,195-197, 1981, Advances in Applied Mathematics, 2, 482-489, 1981.
33. Taga, T., Hibin M., Hirata, Y., Yamasaki, K., Yasukawa, K., Matsuda, T., Hirano, T. and Kishimoto, T. Cell 1989 58, 573-581.
34. Toulmond, S., Vige, X., Fage, D., and Benavides, J. Neurosci Lett 1992, 144, 49-52.
35. Ward L D, Howlett G J, Discolo G, Yasukawa K, Hammacher A, Moritz R L and Simpson R J. High affinity interleukin-6 receptor is a hexameric complex consisting of two molecules each of interleukin-6, interleukin-6 receptor and gp130. J. Biol. Chem. 1994, 269: 23286-23289.
36. Yamada, M., and Hatanaka, H.: Brain Res 1994, 643, 173-80.
37. Zilberstein et al, EMBO J 5:2529 (1986)

The invention claimed is:

1. A method for treating diabetic neuropathy, comprising administering an effective amount of a substance signalling through gp130 to a patient in need thereof, wherein said substance is:
   a) interleukin-6 (IL-6);
   b) a fragment of a) which binds to gp80 and initiates signaling through gp130;
   c) a variant of a) which has at least 90% sequence identity with a) and which initiates signaling through gp130; or
   d) a salt or functional derivative of a), b) or c) which initiates signaling through gp130.

2. A method according to claim 1, wherein the functional derivative comprises at least one moiety attached to one or more functional groups which occur as one or more side chains on the amino acid residues.

3. A method according to claim 2, wherein the moiety is a polyethylene moiety.

4. A method according to claim 1, wherein the substance signaling through gp130 is administered in an amount ranging from about 0.1 to 1000 µg/kg.

5. A method according to claim 4, wherein the substance signaling through gp130 is administered in an amount of about 1 µg/kg or 3 µg/kg or 10 µg/kg or 30 µg/kg.

6. A method according to claim 4, wherein the substance signaling through gp130 is used in an amount ranging from about 1 to 500 µg/kg.

7. A method according to claim 4, wherein the substance signaling through gp130 is administered in an amount ranging from about 0.1 to 100 µg/kg.

8. A method according to claim 1, wherein the substance signaling through gp130 is administered daily.

9. A method according to claim 1, wherein the substance signaling through gp130 is administered three times per week.

10. A method according to claim 1, wherein the substance signaling through gp130 is administered once a week.

11. A method according to claim 1, wherein the diabetic neuropathy is a polyneuropathy.

12. A method according to claim 1, wherein the diabetic neuropathy is a mononeuropathy.

13. A method according to claim 1, wherein the substance is glycosylated at one or more sites.

14. A method according to claim 1, wherein the substance is not glycosylated.

15. A method in accordance with claim 1, wherein said substance is IL-6.

16. A method in accordance with claim 15, wherein said IL-6 is administered in an amount of about 1, 3, 10 or 30 µg/kg.

17. A method according to claim 15, wherein said IL-6 is recombinant IL-6.

* * * * *